United States Patent
Rammensee et al.

(10) Patent No.: US 10,377,797 B2
(45) Date of Patent: Aug. 13, 2019

(54) CELL EPITOPES AND COMBINATION OF CELL EPITOPES FOR USE IN THE IMMUNOTHERAPY OF MYELOMA AND OTHER CANCERS

(71) Applicant: Immatics Biotechnologies GmbH, Tuebingen (DE)

(72) Inventors: Hans-Georg Rammensee, Unterjesingen (DE); Juliane Stickel, Tuebingen (DE); Daniel Johannes Kowalewski, Tuebingen (DE); Stefan Stevanovic, Tuebingen (DE); Simon Walz, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/196,812

(22) Filed: Nov. 20, 2018

(65) Prior Publication Data
US 2019/0077832 A1    Mar. 14, 2019

Related U.S. Application Data

(63) Continuation of application No. 15/191,895, filed on Jun. 24, 2016, now Pat. No. 10,196,422.

(60) Provisional application No. 62/184,500, filed on Jun. 25, 2015.

(30) Foreign Application Priority Data

Jun. 25, 2015 (GB) .................................. 1511191.7

(51) Int. Cl.
| C07K 7/06 | (2006.01) |
| A61K 38/00 | (2006.01) |
| G01N 33/53 | (2006.01) |
| G01N 33/574 | (2006.01) |
| C07K 14/705 | (2006.01) |
| A61K 35/17 | (2015.01) |
| A61K 39/00 | (2006.01) |
| C07K 16/30 | (2006.01) |
| C12N 5/0783 | (2010.01) |
| C07K 16/00 | (2006.01) |
| C07K 7/08 | (2006.01) |

(52) U.S. Cl.
CPC ............... *C07K 7/06* (2013.01); *A61K 35/17* (2013.01); *A61K 38/00* (2013.01); *A61K 39/0011* (2013.01); *C07K 7/08* (2013.01); *C07K 14/705* (2013.01); *C07K 16/00* (2013.01); *C07K 16/30* (2013.01); *C12N 5/0636* (2013.01); *G01N 33/5308* (2013.01); *G01N 33/574* (2013.01); *A61K 2039/5158* (2013.01); *C12N 2800/00* (2013.01)

(58) Field of Classification Search
None
See application file for complete search history.

(56) References Cited

U.S. PATENT DOCUMENTS

| 9,023,803 | B2 | 5/2015 | Singh et al. | |
| 9,056,069 | B2 | 6/2015 | Singh et al. | |
| 2007/0009501 | A1 | 1/2007 | Gires et al. | |
| 2007/0037206 | A1 | 2/2007 | Rosen et al. | |
| 2009/0274714 | A1 | 11/2009 | Singh et al. | |
| 2010/0009463 | A1* | 1/2010 | Hornbeck | C07B 59/008 436/501 |
| 2010/0209427 | A1* | 8/2010 | Li | C12Q 1/48 424/139.1 |
| 2013/0096016 | A1 | 4/2013 | Weinschenk et al. | |
| 2013/0177525 | A1 | 7/2013 | Singh et al. | |

FOREIGN PATENT DOCUMENTS

| EP | 1760089 A1 | 3/2007 |
| WO | 2005/061537 A2 | 7/2005 |
| WO | 2008/009004 A2 | 1/2008 |
| WO | 2011151403 A | 4/2008 |
| WO | 2011/119484 A1 | 9/2011 |
| WO | 2014200910 A2 | 12/2014 |

OTHER PUBLICATIONS

Great Britain Search Report dated Apr. 15, 2016 in counterpart Great Britain Application No. GB1511191.7.
Steffen, W. et al., "Multipeptide immune response to cancer vaccine IMA901 after single-dose cyclophosphamide associates with longer patient survival" Nature Medicine, (2012) vol. 18: 1254-1265.
Janeway CA Jr, Travers P, Walport M, et al. Immunobiology: The Immune System in Health and Disease. 5th edition. New York: Garland Science; 2001. Antigen recognition by T cells. Available from: https://www.ncbi.nlm.nih.gov/books/NBK27098/ (Year: 2001).
International Search Report for PCT/EP2016/064317, dated Dec. 21, 2016.

\* cited by examiner

*Primary Examiner* — Peter J Reddig
(74) *Attorney, Agent, or Firm* — McBee Moore Woodward & Vanik IP, LLC

(57) ABSTRACT

The present invention relates to peptides, proteins, nucleic acids and cells for use in immunotherapeutic methods. In particular, the present invention relates to the immunotherapy of cancer, in particular myeloma. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

25 Claims, 12 Drawing Sheets
(9 of 12 Drawing Sheet(s) Filed in Color)
Specification includes a Sequence Listing.

Ligandome defined myeloma-associated antigens

☐ MCL
▨ Primary MM+MCL

Myeloma-associated antigens (literature)

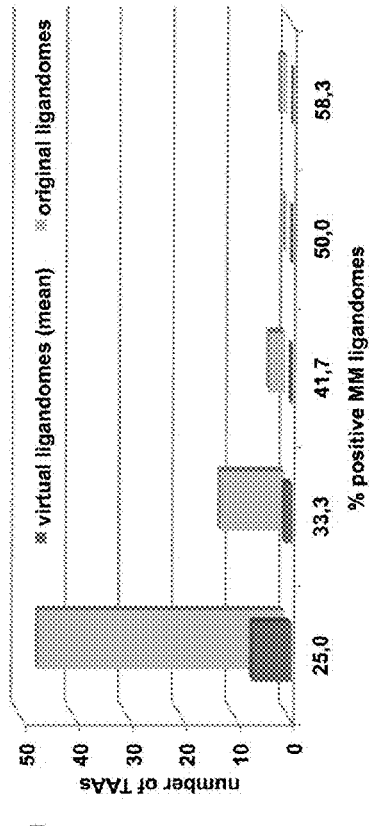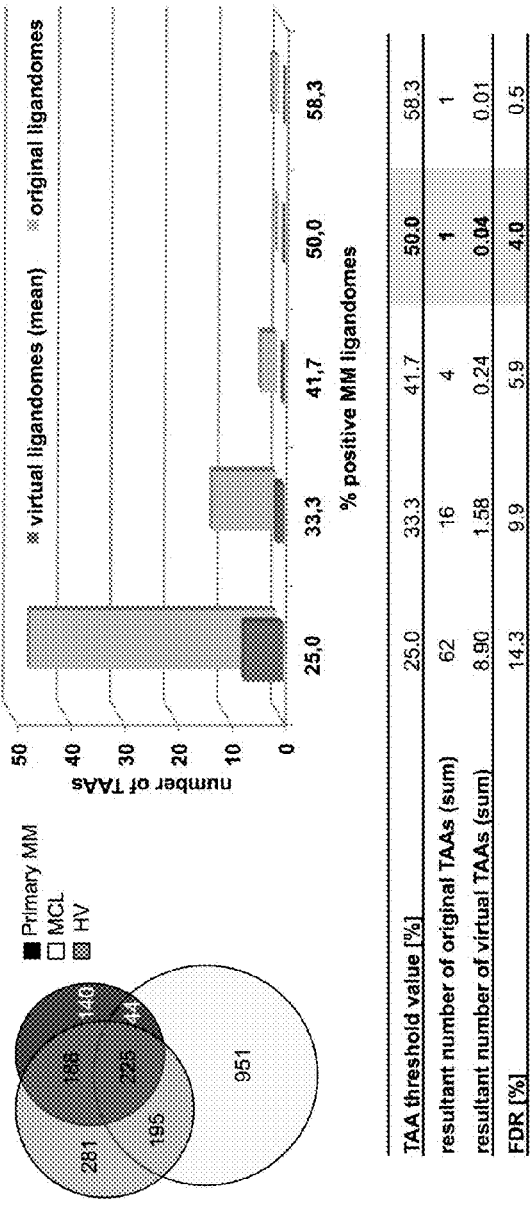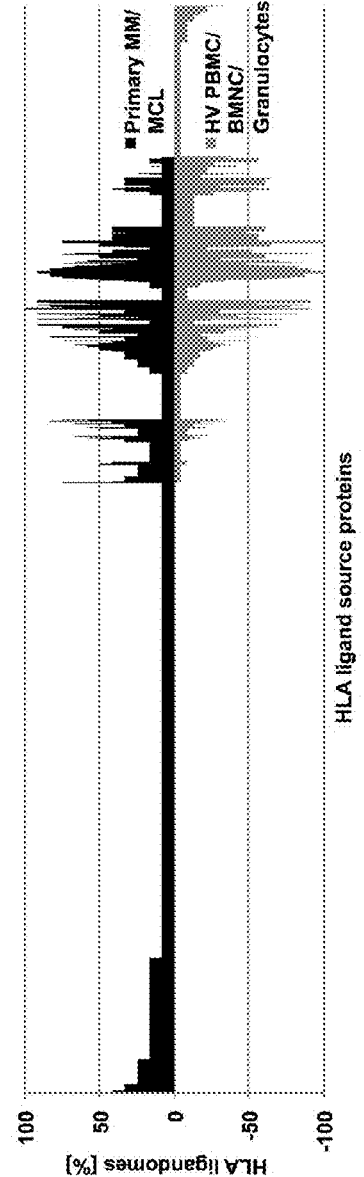
Figure 4A
Figure 4B
Figure 4C

Figure 4D

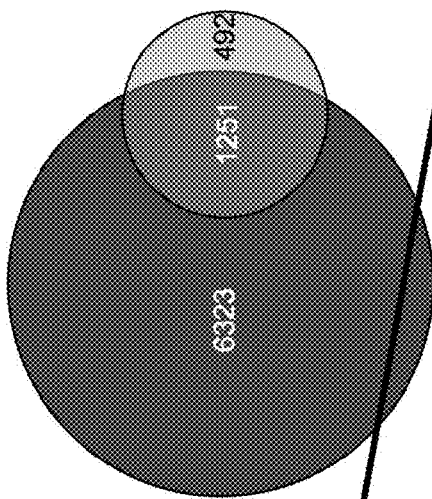

TAAs — HLA class I  
MM-exclusive antigens — HLA class II

Figure 4F

HLA ligand source proteins  
HLA class I | HLA class II

| Synergistic MM antigens | Number of HLA class II ligands | Number of positive MM samples [rep. frequency %] | Peptide | CD4+ T-cell response in MM |
|---|---|---|---|---|
| SLC1A5 | 9 | 2 [13.3] | APVGImFLVAGKIVE | 1/5 (20%) |
| NPC1 | 4 | 2 [13.3] | mPDDSYmVDYFKSISQ | 0/5 (0%) |
| PDIA4 | 8 | 2 [13.3] | GYPTIKILKKGQAVDYEG | 2/5 (40%) |
| KDELR2 | 7 | 2 [13.3] | VPVGGLSFLVNHDFSPL | 2/5 (40%) |
| SLC1A4 | 2 | 1 [6.7] | IVDRTTTVVNVEG | 2/5 (40%) |
| SERPINH1 | 1 | 1 [6.7] | n.t. | n.t. |

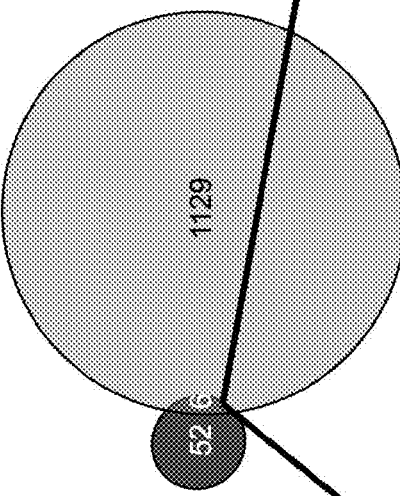

Figure 5A
| Peptide | Sequence | Source protein | HLA | CD8+ T-cell response in MM | Allotype matched presentation in primary MM samples [%] |
|---|---|---|---|---|---|
| P₁ | KAMEAASSL | MMSET | A*02 | 2/16 (12.5%) | 20.0 |
| P₂ | SILEQGLVEA | MMSET | A*02 | 1/8 (12.5%) | 20.0 |
| P₃ | FVFPGELLL | SLC1A5 | A*02 | 2/14 (14.3%) | 20.0 |
| P₄ | FLFQLLCLL | SEMA4A | A*02 | 1/14 (7.1%) | 20.0 |
| P₅ | LPPPHVPL | SLX1A | B*07 | 1/6 (25.0%) | 25.0 |
| P₆ | LAHVGPRL | SLX1A | A*02 | 2/14 (14.3%) | 20.0 |
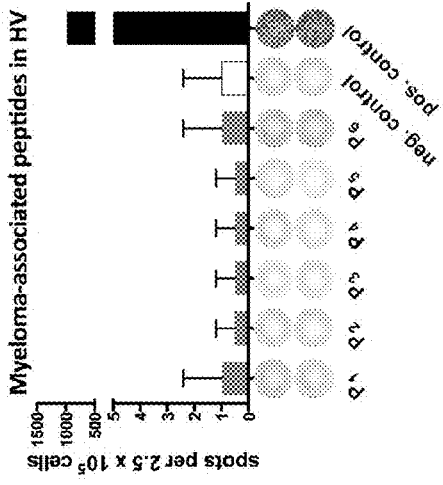
Figure 5B
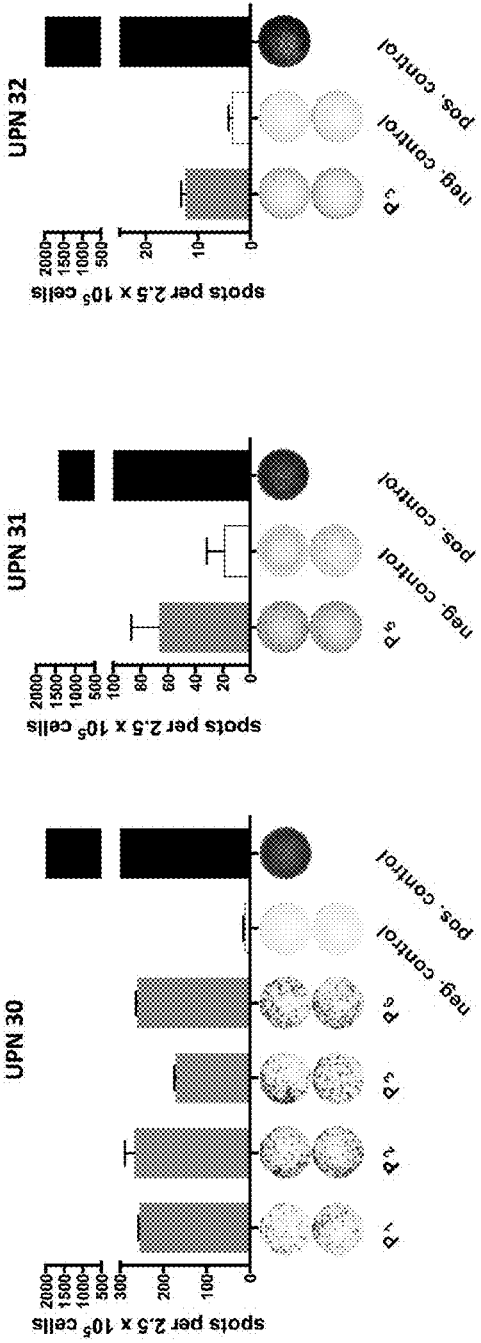
Figure 5C

SEQ ID NO: 107

SEQ ID NO: 177

SEQUENCE LISTING

```
<160> NUMBER OF SEQ ID NOS: 237

<210> SEQ ID NO 1
<211> LENGTH: 9
<212> TYPE: PRT
<213> ORGANISM: Homo sapiens

<400> SEQUENCE: 1

Ala Ala Ser Pro Val Val Ala Glu Tyr
1               5

<210> SEQ ID NO 2
<211> LENGTH: 10
<212> TYPE: PRT
<213> ORGANISM: Homo sapiens

<400> SEQUENCE: 2

Ala Glu Asn Ala Pro Ser Lys Glu Val Leu
1               5                   10

<210> SEQ ID NO 3
<211> LENGTH: 10
<212> TYPE: PRT
<213> ORGANISM: Homo sapiens

<400> SEQUENCE: 3

Ala Glu Gln Glu Ile Ala Arg Leu Val Leu
1               5                   10

<210> SEQ ID NO 4
<211> LENGTH: 11
<212> TYPE: PRT
<213> ORGANISM: Homo sapiens

<400> SEQUENCE: 4

Ala Phe Ile Gln Ala Gly Ile Phe Gln Glu Phe
1               5                   10

<210> SEQ ID NO 5
<211> LENGTH: 9
<212> TYPE: PRT
<213> ORGANISM: Homo sapiens

<400> SEQUENCE: 5

Ala His Ser Glu Gln Leu Gln Ala Leu
1               5

<210> SEQ ID NO 6
<211> LENGTH: 13
<212> TYPE: PRT
<213> ORGANISM: Homo sapiens

<400> SEQUENCE: 6
```

Ala Ile Ile Leu Glu Ala Val Asn Leu Pro Val Asp His
1               5                   10

<210> SEQ ID NO 7
<211> LENGTH: 9
<212> TYPE: PRT
<213> ORGANISM: Homo sapiens

<400> SEQUENCE: 7

Ala Lys Arg Phe Asp Val Ser Gly Tyr
1               5

<210> SEQ ID NO 8
<211> LENGTH: 11
<212> TYPE: PRT
<213> ORGANISM: Homo sapiens

<400> SEQUENCE: 8

Ala Leu Asp Pro Leu Ala Asp Lys Ile Leu Ile
1               5                   10

<210> SEQ ID NO 9
<211> LENGTH: 9
<212> TYPE: PRT
<213> ORGANISM: Homo sapiens

<400> SEQUENCE: 9

Ala Leu Lys Lys Pro Ile Lys Gly Lys
1               5

<210> SEQ ID NO 10
<211> LENGTH: 9
<212> TYPE: PRT
<213> ORGANISM: Homo sapiens

<400> SEQUENCE: 10

Ala Leu Trp Gly Arg Thr Thr Leu Lys
1               5

<210> SEQ ID NO 11
<211> LENGTH: 10
<212> TYPE: PRT
<213> ORGANISM: Homo sapiens

<400> SEQUENCE: 11

Ala Pro Phe Gln Gly Asp Gln Arg Ser Leu
1               5                   10

<210> SEQ ID NO 12
<211> LENGTH: 10
<212> TYPE: PRT
<213> ORGANISM: Homo sapiens

<400> SEQUENCE: 12

Ala Pro Lys Tyr Gly Ser Tyr Asn Val Phe
1               5                   10

<210> SEQ ID NO 13
<211> LENGTH: 10
<212> TYPE: PRT
<213> ORGANISM: Homo sapiens

<400> SEQUENCE: 13

Ala Pro Arg His Pro Ser Thr Asn Ser Leu
1               5                   10

<210> SEQ ID NO 14
<211> LENGTH: 11
<212> TYPE: PRT
<213> ORGANISM: Homo sapiens

<400> SEQUENCE: 14

Ala Pro Arg His Pro Ser Thr Asn Ser Leu Leu
1               5                   10

<210> SEQ ID NO 15
<211> LENGTH: 14
<212> TYPE: PRT
<213> ORGANISM: Homo sapiens

<400> SEQUENCE: 15

Ala Pro Val Gly Ile Met Phe Leu Val Ala Gly Lys Ile Val
1               5                   10

<210> SEQ ID NO 16
<211> LENGTH: 15
<212> TYPE: PRT
<213> ORGANISM: Homo sapiens

<400> SEQUENCE: 16

Ala Pro Val Gly Ile Met Phe Leu Val Ala Gly Lys Ile Val Glu
1               5                   10                  15

<210> SEQ ID NO 17
<211> LENGTH: 11
<212> TYPE: PRT
<213> ORGANISM: Homo sapiens

<400> SEQUENCE: 17

Ala Ser Asn Pro Ser Asn Pro Arg Pro Ser Lys
1               5                   10

<210> SEQ ID NO 18
<211> LENGTH: 14
<212> TYPE: PRT
<213> ORGANISM: Homo sapiens

<400> SEQUENCE: 18

Ala Val Phe Ile Ala Gln Leu Ser Gln Gln Ser Leu Asp Phe
1               5                   10

<210> SEQ ID NO 19
<211> LENGTH: 11
<212> TYPE: PRT
<213> ORGANISM: Homo sapiens

<400> SEQUENCE: 19

Asp Ala Leu Gly Ala Gly Ile Leu His His Leu
1               5                   10

<210> SEQ ID NO 20
<211> LENGTH: 8
<212> TYPE: PRT
<213> ORGANISM: Homo sapiens

<400> SEQUENCE: 20

Asp Glu Val Leu Leu Gln Lys Leu
1               5

```
<210> SEQ ID NO 21
<211> LENGTH: 19
<212> TYPE: PRT
<213> ORGANISM: Homo sapiens

<400> SEQUENCE: 21

Asp Gly Asp Asp Val Ile Ile Ile Gly Val Phe Lys Gly Glu Ser Asp
1               5                   10                  15

Pro Ala Tyr

<210> SEQ ID NO 22
<211> LENGTH: 11
<212> TYPE: PRT
<213> ORGANISM: Homo sapiens

<400> SEQUENCE: 22

Asp Ile Lys Asp Thr Asp Val Ile Met Lys Arg
1               5                   10

<210> SEQ ID NO 23
<211> LENGTH: 9
<212> TYPE: PRT
<213> ORGANISM: Homo sapiens

<400> SEQUENCE: 23

Asp Ile Gln Asp Pro Gly Val Pro Arg
1               5

<210> SEQ ID NO 24
<211> LENGTH: 11
<212> TYPE: PRT
<213> ORGANISM: Homo sapiens

<400> SEQUENCE: 24

Asp Leu Phe Arg Tyr Asn Pro Tyr Leu Lys Arg
1               5                   10

<210> SEQ ID NO 25
<211> LENGTH: 9
<212> TYPE: PRT
<213> ORGANISM: Homo sapiens

<400> SEQUENCE: 25

Asp Leu Leu Asp Gly Phe Ile Ala Arg
1               5

<210> SEQ ID NO 26
<211> LENGTH: 9
<212> TYPE: PRT
<213> ORGANISM: Homo sapiens

<400> SEQUENCE: 26

Asp Leu Asn Phe Pro Glu Ile Lys Arg
1               5

<210> SEQ ID NO 27
<211> LENGTH: 11
<212> TYPE: PRT
<213> ORGANISM: Homo sapiens

<400> SEQUENCE: 27

Asp Leu Arg Pro Ala Thr Asp Tyr His Val Arg
1               5                   10
```

```
<210> SEQ ID NO 28
<211> LENGTH: 9
<212> TYPE: PRT
<213> ORGANISM: Homo sapiens

<400> SEQUENCE: 28

Asp Arg Tyr Leu Leu Gly Thr Ser Leu
1               5

<210> SEQ ID NO 29
<211> LENGTH: 9
<212> TYPE: PRT
<213> ORGANISM: Homo sapiens

<400> SEQUENCE: 29

Asp Ser Phe Glu Arg Ser Asn Ser Leu
1               5

<210> SEQ ID NO 30
<211> LENGTH: 12
<212> TYPE: PRT
<213> ORGANISM: Homo sapiens

<400> SEQUENCE: 30

Asp Thr Gln Ser Gly Ser Leu Leu Phe Ile Gly Arg
1               5                   10

<210> SEQ ID NO 31
<211> LENGTH: 9
<212> TYPE: PRT
<213> ORGANISM: Homo sapiens

<400> SEQUENCE: 31

Asp Val Ala Glu Pro Tyr Lys Val Tyr
1               5

<210> SEQ ID NO 32
<211> LENGTH: 9
<212> TYPE: PRT
<213> ORGANISM: Homo sapiens

<400> SEQUENCE: 32

Asp Val Asn Asn Ile Gly Lys Tyr Arg
1               5

<210> SEQ ID NO 33
<211> LENGTH: 9
<212> TYPE: PRT
<213> ORGANISM: Homo sapiens

<400> SEQUENCE: 33

Asp Val Pro Asp His Ile Ile Ala Tyr
1               5

<210> SEQ ID NO 34
<211> LENGTH: 16
<212> TYPE: PRT
<213> ORGANISM: Homo sapiens

<400> SEQUENCE: 34

Glu Gly Asn Pro Leu Leu Lys His Tyr Arg Gly Pro Ala Gly Asp Ala
1               5                   10                  15

<210> SEQ ID NO 35
<211> LENGTH: 17
```

```
<212> TYPE: PRT
<213> ORGANISM: Homo sapiens

<400> SEQUENCE: 35

Glu Gly Asn Pro Leu Leu Lys His Tyr Arg Gly Pro Ala Gly Asp Ala
1               5                   10                  15

Thr

<210> SEQ ID NO 36
<211> LENGTH: 9
<212> TYPE: PRT
<213> ORGANISM: Homo sapiens

<400> SEQUENCE: 36

Glu Ile Ile Glu Lys Asn Phe Asp Tyr
1               5

<210> SEQ ID NO 37
<211> LENGTH: 11
<212> TYPE: PRT
<213> ORGANISM: Homo sapiens

<400> SEQUENCE: 37

Glu Ile Ile Glu Lys Asn Phe Asp Tyr Leu Arg
1               5                   10

<210> SEQ ID NO 38
<211> LENGTH: 9
<212> TYPE: PRT
<213> ORGANISM: Homo sapiens

<400> SEQUENCE: 38

Glu Ile Thr Glu Val Ala Leu Glu Tyr
1               5

<210> SEQ ID NO 39
<211> LENGTH: 16
<212> TYPE: PRT
<213> ORGANISM: Homo sapiens

<400> SEQUENCE: 39

Glu Asn Gly Val Leu Val Leu Asn Asp Ala Asn Phe Asp Asn Phe Val
1               5                   10                  15

<210> SEQ ID NO 40
<211> LENGTH: 10
<212> TYPE: PRT
<213> ORGANISM: Homo sapiens

<400> SEQUENCE: 40

Glu Gln Leu Tyr Asp Leu Thr Leu Glu Tyr
1               5                   10

<210> SEQ ID NO 41
<211> LENGTH: 9
<212> TYPE: PRT
<213> ORGANISM: Homo sapiens

<400> SEQUENCE: 41

Glu Arg Phe Glu Lys Thr Phe Gln Leu
1               5

<210> SEQ ID NO 42
<211> LENGTH: 8
```

```
<212> TYPE: PRT
<213> ORGANISM: Homo sapiens

<400> SEQUENCE: 42

Glu Tyr Gly His Ile Pro Ser Phe
1               5

<210> SEQ ID NO 43
<211> LENGTH: 10
<212> TYPE: PRT
<213> ORGANISM: Homo sapiens

<400> SEQUENCE: 43

Phe Ala Gln Ile Ile Ser Val Ala Leu Ile
1               5                   10

<210> SEQ ID NO 44
<211> LENGTH: 9
<212> TYPE: PRT
<213> ORGANISM: Homo sapiens

<400> SEQUENCE: 44

Phe Ala Tyr Pro Ala Ile Arg Tyr Leu
1               5

<210> SEQ ID NO 45
<211> LENGTH: 10
<212> TYPE: PRT
<213> ORGANISM: Homo sapiens

<400> SEQUENCE: 45

Phe Phe Lys Pro His Trp Asp Glu Lys Phe
1               5                   10

<210> SEQ ID NO 46
<211> LENGTH: 9
<212> TYPE: PRT
<213> ORGANISM: Homo sapiens

<400> SEQUENCE: 46

Phe Ile Ser Gly His Thr Ser Glu Leu
1               5

<210> SEQ ID NO 47
<211> LENGTH: 9
<212> TYPE: PRT
<213> ORGANISM: Homo sapiens

<400> SEQUENCE: 47

Phe Lys Ser Pro Ala Ala Ser Ser Phe
1               5

<210> SEQ ID NO 48
<211> LENGTH: 9
<212> TYPE: PRT
<213> ORGANISM: Homo sapiens

<400> SEQUENCE: 48

Phe Leu Phe Gln Leu Leu Gln Leu Leu
1               5

<210> SEQ ID NO 49
<211> LENGTH: 10
<212> TYPE: PRT
<213> ORGANISM: Homo sapiens
```

<400> SEQUENCE: 49

Phe Leu Trp Asp Glu Gly Phe His Gln Leu
1               5                   10

<210> SEQ ID NO 50
<211> LENGTH: 9
<212> TYPE: PRT
<213> ORGANISM: Homo sapiens

<400> SEQUENCE: 50

Phe Asn Phe Leu Arg Asn Val Ser Leu
1               5

<210> SEQ ID NO 51
<211> LENGTH: 9
<212> TYPE: PRT
<213> ORGANISM: Homo sapiens

<400> SEQUENCE: 51

Phe Val Phe Pro Gly Glu Leu Leu Leu
1               5

<210> SEQ ID NO 52
<211> LENGTH: 9
<212> TYPE: PRT
<213> ORGANISM: Homo sapiens

<400> SEQUENCE: 52

Gly Ala Lys Ala Ser Thr Thr Ser Leu
1               5

<210> SEQ ID NO 53
<211> LENGTH: 9
<212> TYPE: PRT
<213> ORGANISM: Homo sapiens

<400> SEQUENCE: 53

Gly Glu Leu Ile Glu Val Val His Leu
1               5

<210> SEQ ID NO 54
<211> LENGTH: 9
<212> TYPE: PRT
<213> ORGANISM: Homo sapiens

<400> SEQUENCE: 54

Gly Glu Thr Ala Phe Ala Phe His Leu
1               5

<210> SEQ ID NO 55
<211> LENGTH: 9
<212> TYPE: PRT
<213> ORGANISM: Homo sapiens

<400> SEQUENCE: 55

Gly Glu Val Ala Pro Ser Met Phe Leu
1               5

<210> SEQ ID NO 56
<211> LENGTH: 10
<212> TYPE: PRT
<213> ORGANISM: Homo sapiens

<400> SEQUENCE: 56

Gly Glu Val Gln Asp Leu Leu Val Arg Leu
1               5                   10

<210> SEQ ID NO 57
<211> LENGTH: 9
<212> TYPE: PRT
<213> ORGANISM: Homo sapiens

<400> SEQUENCE: 57

Gly Lys Val Gln Glu Asn Ser Ala Tyr
1               5

<210> SEQ ID NO 58
<211> LENGTH: 9
<212> TYPE: PRT
<213> ORGANISM: Homo sapiens

<400> SEQUENCE: 58

Gly Lys Tyr Ile Phe Ala Ser Ile Leu
1               5

<210> SEQ ID NO 59
<211> LENGTH: 15
<212> TYPE: PRT
<213> ORGANISM: Homo sapiens

<400> SEQUENCE: 59

Gly Asn Pro Leu Leu Lys His Tyr Arg Gly Pro Ala Gly Asp Ala
1               5                   10                  15

<210> SEQ ID NO 60
<211> LENGTH: 9
<212> TYPE: PRT
<213> ORGANISM: Homo sapiens

<400> SEQUENCE: 60

Gly Pro Phe Ser Gln Phe Ile Lys Ala
1               5

<210> SEQ ID NO 61
<211> LENGTH: 10
<212> TYPE: PRT
<213> ORGANISM: Homo sapiens

<400> SEQUENCE: 61

Gly Pro Arg Pro Ile Thr Gln Ser Glu Leu
1               5                   10

<210> SEQ ID NO 62
<211> LENGTH: 9
<212> TYPE: PRT
<213> ORGANISM: Homo sapiens

<400> SEQUENCE: 62

Gly Arg Tyr Pro Gly Val Ser Asn Tyr
1               5

<210> SEQ ID NO 63
<211> LENGTH: 17
<212> TYPE: PRT
<213> ORGANISM: Homo sapiens

<400> SEQUENCE: 63

Gly Tyr Pro Thr Ile Lys Ile Leu Lys Lys Gly Gln Ala Val Asp Tyr

```
<210> SEQ ID NO 64
<211> LENGTH: 18
<212> TYPE: PRT
<213> ORGANISM: Homo sapiens

<400> SEQUENCE: 64

Gly Tyr Pro Thr Ile Lys Ile Leu Lys Lys Gly Gln Ala Val Asp Tyr
1               5                   10                  15
Glu Gly

<210> SEQ ID NO 65
<211> LENGTH: 9
<212> TYPE: PRT
<213> ORGANISM: Homo sapiens

<400> SEQUENCE: 65

His Pro Lys Gln Pro Glu Pro Ser Ala
1               5

<210> SEQ ID NO 66
<211> LENGTH: 10
<212> TYPE: PRT
<213> ORGANISM: Homo sapiens

<400> SEQUENCE: 66

His Pro Lys Gln Pro Glu Pro Ser Ala Thr
1               5                   10

<210> SEQ ID NO 67
<211> LENGTH: 9
<212> TYPE: PRT
<213> ORGANISM: Homo sapiens

<400> SEQUENCE: 67

His Ser Met Asp Phe Val Ala Tyr Arg
1               5

<210> SEQ ID NO 68
<211> LENGTH: 9
<212> TYPE: PRT
<213> ORGANISM: Homo sapiens

<400> SEQUENCE: 68

Ile Ala Asp Pro Phe Phe Arg Ser Ala
1               5

<210> SEQ ID NO 69
<211> LENGTH: 9
<212> TYPE: PRT
<213> ORGANISM: Homo sapiens

<400> SEQUENCE: 69

Ile Glu His Pro Ser Met Ser Val Tyr
1               5

<210> SEQ ID NO 70
<211> LENGTH: 9
<212> TYPE: PRT
<213> ORGANISM: Homo sapiens

<400> SEQUENCE: 70
```

```
Ile Glu Ser His Pro Asp Asn Ala Leu
1               5

<210> SEQ ID NO 71
<211> LENGTH: 8
<212> TYPE: PRT
<213> ORGANISM: Homo sapiens

<400> SEQUENCE: 71

Ile Glu Val Glu Ala Val Arg Phe
1               5

<210> SEQ ID NO 72
<211> LENGTH: 9
<212> TYPE: PRT
<213> ORGANISM: Homo sapiens

<400> SEQUENCE: 72

Ile His Ile Leu Asp Val Leu Val Leu
1               5

<210> SEQ ID NO 73
<211> LENGTH: 9
<212> TYPE: PRT
<213> ORGANISM: Homo sapiens

<400> SEQUENCE: 73

Ile Ile Phe Asp Arg Pro Leu Leu Tyr
1               5

<210> SEQ ID NO 74
<211> LENGTH: 10
<212> TYPE: PRT
<213> ORGANISM: Homo sapiens

<400> SEQUENCE: 74

Ile Leu Arg Asp Gly Ile Thr Ala Gly Lys
1               5                   10

<210> SEQ ID NO 75
<211> LENGTH: 9
<212> TYPE: PRT
<213> ORGANISM: Homo sapiens

<400> SEQUENCE: 75

Ile Leu Trp Glu Thr Val Pro Ser Met
1               5

<210> SEQ ID NO 76
<211> LENGTH: 9
<212> TYPE: PRT
<213> ORGANISM: Homo sapiens

<400> SEQUENCE: 76

Ile Pro Ala Lys Pro Pro Val Ser Phe
1               5

<210> SEQ ID NO 77
<211> LENGTH: 10
<212> TYPE: PRT
<213> ORGANISM: Homo sapiens

<400> SEQUENCE: 77

Ile Pro Ala Lys Pro Pro Val Ser Phe Phe
```

<210> SEQ ID NO 78
<211> LENGTH: 9
<212> TYPE: PRT
<213> ORGANISM: Homo sapiens

<400> SEQUENCE: 78

Ile Gln Ala Gly Ile Phe Gln Glu Phe
1               5

<210> SEQ ID NO 79
<211> LENGTH: 8
<212> TYPE: PRT
<213> ORGANISM: Homo sapiens

<400> SEQUENCE: 79

Ile Gln Ile Leu His Gln Val Leu
1               5

<210> SEQ ID NO 80
<211> LENGTH: 13
<212> TYPE: PRT
<213> ORGANISM: Homo sapiens

<400> SEQUENCE: 80

Ile Val Asp Arg Thr Thr Thr Val Val Asn Val Glu Gly
1               5                   10

<210> SEQ ID NO 81
<211> LENGTH: 15
<212> TYPE: PRT
<213> ORGANISM: Homo sapiens

<400> SEQUENCE: 81

Ile Val Asp Arg Thr Thr Thr Val Val Asn Val Glu Gly Asp Ala
1               5                   10                  15

<210> SEQ ID NO 82
<211> LENGTH: 9
<212> TYPE: PRT
<213> ORGANISM: Homo sapiens

<400> SEQUENCE: 82

Lys Ala Met Glu Ala Ala Ser Ser Leu
1               5

<210> SEQ ID NO 83
<211> LENGTH: 9
<212> TYPE: PRT
<213> ORGANISM: Homo sapiens

<400> SEQUENCE: 83

Lys Ala Val Asn Pro Gly Arg Ser Leu
1               5

<210> SEQ ID NO 84
<211> LENGTH: 10
<212> TYPE: PRT
<213> ORGANISM: Homo sapiens

<400> SEQUENCE: 84

Lys Asp Ala Arg Lys Gly Pro Leu Val Pro
1               5                   10

<210> SEQ ID NO 85
<211> LENGTH: 9
<212> TYPE: PRT
<213> ORGANISM: Homo sapiens

<400> SEQUENCE: 85

Lys Glu Glu Asn Gly Val Leu Val Leu
1               5

<210> SEQ ID NO 86
<211> LENGTH: 9
<212> TYPE: PRT
<213> ORGANISM: Homo sapiens

<400> SEQUENCE: 86

Lys Glu Phe Ala Ala Ile Val Asp Val
1               5

<210> SEQ ID NO 87
<211> LENGTH: 10
<212> TYPE: PRT
<213> ORGANISM: Homo sapiens

<400> SEQUENCE: 87

Lys Glu Gly Leu Ile Leu Pro Glu Thr Leu
1               5                   10

<210> SEQ ID NO 88
<211> LENGTH: 9
<212> TYPE: PRT
<213> ORGANISM: Homo sapiens

<400> SEQUENCE: 88

Lys Ile Leu Lys Pro Val Lys Lys Lys
1               5

<210> SEQ ID NO 89
<211> LENGTH: 10
<212> TYPE: PRT
<213> ORGANISM: Homo sapiens

<400> SEQUENCE: 89

Lys Leu Gly Trp Leu Ser Ser Met Thr Lys
1               5                   10

<210> SEQ ID NO 90
<211> LENGTH: 10
<212> TYPE: PRT
<213> ORGANISM: Homo sapiens

<400> SEQUENCE: 90

Lys Leu Pro Leu Pro Leu Pro Pro Arg Leu
1               5                   10

<210> SEQ ID NO 91
<211> LENGTH: 9
<212> TYPE: PRT
<213> ORGANISM: Homo sapiens

<400> SEQUENCE: 91

Lys Leu Arg Glu Leu Thr Gln Arg Tyr
1               5

<210> SEQ ID NO 92

```
<211> LENGTH: 9
<212> TYPE: PRT
<213> ORGANISM: Homo sapiens

<400> SEQUENCE: 92

Lys Leu Ser Ser Leu Ile Ile Leu Met
1               5

<210> SEQ ID NO 93
<211> LENGTH: 10
<212> TYPE: PRT
<213> ORGANISM: Homo sapiens

<400> SEQUENCE: 93

Lys Pro Lys Asp Pro Leu Lys Ile Ser Leu
1               5                   10

<210> SEQ ID NO 94
<211> LENGTH: 9
<212> TYPE: PRT
<213> ORGANISM: Homo sapiens

<400> SEQUENCE: 94

Lys Pro Gln Pro Arg Pro Gln Thr Leu
1               5

<210> SEQ ID NO 95
<211> LENGTH: 8
<212> TYPE: PRT
<213> ORGANISM: Homo sapiens

<400> SEQUENCE: 95

Lys Pro Arg Pro Pro Gln Gly Leu
1               5

<210> SEQ ID NO 96
<211> LENGTH: 10
<212> TYPE: PRT
<213> ORGANISM: Homo sapiens

<400> SEQUENCE: 96

Lys Pro Arg Pro Pro Gln Gly Leu Val Arg
1               5                   10

<210> SEQ ID NO 97
<211> LENGTH: 9
<212> TYPE: PRT
<213> ORGANISM: Homo sapiens

<400> SEQUENCE: 97

Lys Pro Ser Thr Lys Ala Leu Val Leu
1               5

<210> SEQ ID NO 98
<211> LENGTH: 11
<212> TYPE: PRT
<213> ORGANISM: Homo sapiens

<400> SEQUENCE: 98

Lys Pro Tyr Pro Asn Ser Glu Ala Ala Arg Ala
1               5                   10

<210> SEQ ID NO 99
<211> LENGTH: 9
<212> TYPE: PRT
```

<213> ORGANISM: Homo sapiens

<400> SEQUENCE: 99

Lys Gln His Gly Ile Pro Ile Pro Val
1               5

<210> SEQ ID NO 100
<211> LENGTH: 9
<212> TYPE: PRT
<213> ORGANISM: Homo sapiens

<400> SEQUENCE: 100

Lys Thr Glu Val His Ile Arg Pro Lys
1               5

<210> SEQ ID NO 101
<211> LENGTH: 9
<212> TYPE: PRT
<213> ORGANISM: Homo sapiens

<400> SEQUENCE: 101

Lys Thr Gln Leu Leu Pro Thr Ser Lys
1               5

<210> SEQ ID NO 102
<211> LENGTH: 10
<212> TYPE: PRT
<213> ORGANISM: Homo sapiens

<400> SEQUENCE: 102

Lys Val Met Leu Ser Ala Leu Gly Met Leu
1               5                   10

<210> SEQ ID NO 103
<211> LENGTH: 9
<212> TYPE: PRT
<213> ORGANISM: Homo sapiens

<400> SEQUENCE: 103

Lys Tyr Glu Ser Ile Arg Leu Leu Phe
1               5

<210> SEQ ID NO 104
<211> LENGTH: 10
<212> TYPE: PRT
<213> ORGANISM: Homo sapiens

<400> SEQUENCE: 104

Lys Tyr Pro Asp Ser His Leu Pro Thr Leu
1               5                   10

<210> SEQ ID NO 105
<211> LENGTH: 9
<212> TYPE: PRT
<213> ORGANISM: Homo sapiens

<400> SEQUENCE: 105

Leu Ala Ala Leu Pro Gly Val Ser Leu
1               5

<210> SEQ ID NO 106
<211> LENGTH: 9
<212> TYPE: PRT
<213> ORGANISM: Homo sapiens

```
<400> SEQUENCE: 106

Leu Ala Asp His Thr Val His Val Leu
1               5

<210> SEQ ID NO 107
<211> LENGTH: 9
<212> TYPE: PRT
<213> ORGANISM: Homo sapiens

<400> SEQUENCE: 107

Leu Ala Phe Pro Gly Glu Met Leu Leu
1               5

<210> SEQ ID NO 108
<211> LENGTH: 8
<212> TYPE: PRT
<213> ORGANISM: Homo sapiens

<400> SEQUENCE: 108

Leu Ala His Val Gly Pro Arg Leu
1               5

<210> SEQ ID NO 109
<211> LENGTH: 8
<212> TYPE: PRT
<213> ORGANISM: Homo sapiens

<400> SEQUENCE: 109

Leu Glu Lys Glu Gly Leu Ile Leu
1               5

<210> SEQ ID NO 110
<211> LENGTH: 9
<212> TYPE: PRT
<213> ORGANISM: Homo sapiens

<400> SEQUENCE: 110

Leu Lys Ile Pro Ile Ser Ile Glu Phe
1               5

<210> SEQ ID NO 111
<211> LENGTH: 10
<212> TYPE: PRT
<213> ORGANISM: Homo sapiens

<400> SEQUENCE: 111

Leu Leu Phe Pro Tyr Ile Leu Pro Pro Lys
1               5                   10

<210> SEQ ID NO 112
<211> LENGTH: 9
<212> TYPE: PRT
<213> ORGANISM: Homo sapiens

<400> SEQUENCE: 112

Leu Leu Arg Phe Ser Gln Asp Asn Ala
1               5

<210> SEQ ID NO 113
<211> LENGTH: 8
<212> TYPE: PRT
<213> ORGANISM: Homo sapiens

<400> SEQUENCE: 113
```

Leu Pro Ala Glu His Gly Val Leu
1               5

<210> SEQ ID NO 114
<211> LENGTH: 10
<212> TYPE: PRT
<213> ORGANISM: Homo sapiens

<400> SEQUENCE: 114

Leu Pro Lys Asp Val Ser Pro Thr Gln Ala
1               5                   10

<210> SEQ ID NO 115
<211> LENGTH: 9
<212> TYPE: PRT
<213> ORGANISM: Homo sapiens

<400> SEQUENCE: 115

Leu Pro Pro Pro Pro His Val Pro Leu
1               5

<210> SEQ ID NO 116
<211> LENGTH: 9
<212> TYPE: PRT
<213> ORGANISM: Homo sapiens

<400> SEQUENCE: 116

Leu Pro Gln Leu His Ser Leu Val Leu
1               5

<210> SEQ ID NO 117
<211> LENGTH: 14
<212> TYPE: PRT
<213> ORGANISM: Homo sapiens

<400> SEQUENCE: 117

Leu Pro Val Leu Leu Ser Tyr Ile Gly Pro Ser Val Asn Lys
1               5                   10

<210> SEQ ID NO 118
<211> LENGTH: 8
<212> TYPE: PRT
<213> ORGANISM: Homo sapiens

<400> SEQUENCE: 118

Leu Arg Phe Ser Gln Asp Asn Ala
1               5

<210> SEQ ID NO 119
<211> LENGTH: 10
<212> TYPE: PRT
<213> ORGANISM: Homo sapiens

<400> SEQUENCE: 119

Leu Tyr Asp Val Ala Gly Gln Gly Tyr Leu
1               5                   10

<210> SEQ ID NO 120
<211> LENGTH: 11
<212> TYPE: PRT
<213> ORGANISM: Homo sapiens

<400> SEQUENCE: 120

Met Asp Leu Gln Pro Gly Asn Ala Leu Lys Arg
1               5                   10

<210> SEQ ID NO 121
<211> LENGTH: 9
<212> TYPE: PRT
<213> ORGANISM: Homo sapiens

<400> SEQUENCE: 121

Met His Gly Gln Pro Ser Pro Ser Leu
1               5

<210> SEQ ID NO 122
<211> LENGTH: 12
<212> TYPE: PRT
<213> ORGANISM: Homo sapiens

<400> SEQUENCE: 122

Met Asn Ile Phe Arg Leu Thr Gly Asp Leu Ser His
1               5                   10

<210> SEQ ID NO 123
<211> LENGTH: 16
<212> TYPE: PRT
<213> ORGANISM: Homo sapiens

<400> SEQUENCE: 123

Met Pro Asp Asp Ser Tyr Met Val Asp Tyr Phe Lys Ser Ile Ser Gln
1               5                   10                  15

<210> SEQ ID NO 124
<211> LENGTH: 17
<212> TYPE: PRT
<213> ORGANISM: Homo sapiens

<400> SEQUENCE: 124

Met Pro Asp Asp Ser Tyr Met Val Asp Tyr Phe Lys Ser Ile Ser Gln
1               5                   10                  15

Tyr

<210> SEQ ID NO 125
<211> LENGTH: 9
<212> TYPE: PRT
<213> ORGANISM: Homo sapiens

<400> SEQUENCE: 125

Met Arg Leu Ser Leu Pro Leu Leu Leu
1               5

<210> SEQ ID NO 126
<211> LENGTH: 10
<212> TYPE: PRT
<213> ORGANISM: Homo sapiens

<400> SEQUENCE: 126

Met Arg Leu Ser Leu Pro Leu Leu Leu Leu
1               5                   10

<210> SEQ ID NO 127
<211> LENGTH: 8
<212> TYPE: PRT
<213> ORGANISM: Homo sapiens

<400> SEQUENCE: 127

Asn Glu Asp Phe Ser Phe His Tyr
1               5

<210> SEQ ID NO 128
<211> LENGTH: 9
<212> TYPE: PRT
<213> ORGANISM: Homo sapiens

<400> SEQUENCE: 128

Asn Glu Phe Pro Val Phe Asp Glu Phe
1               5

<210> SEQ ID NO 129
<211> LENGTH: 9
<212> TYPE: PRT
<213> ORGANISM: Homo sapiens

<400> SEQUENCE: 129

Asn Glu Val Ile Met Thr Ile Gly Phe
1               5

<210> SEQ ID NO 130
<211> LENGTH: 15
<212> TYPE: PRT
<213> ORGANISM: Homo sapiens

<400> SEQUENCE: 130

Asn Gly Val Leu Val Leu Asn Asp Ala Asn Phe Asp Asn Phe Val
1               5                   10                  15

<210> SEQ ID NO 131
<211> LENGTH: 11
<212> TYPE: PRT
<213> ORGANISM: Homo sapiens

<400> SEQUENCE: 131

Asn Ile Gly Gln Lys Glu Asp Phe Glu Glu Ala
1               5                   10

<210> SEQ ID NO 132
<211> LENGTH: 9
<212> TYPE: PRT
<213> ORGANISM: Homo sapiens

<400> SEQUENCE: 132

Asn Met Asp Leu Met Arg Ala Asp Met
1               5

<210> SEQ ID NO 133
<211> LENGTH: 14
<212> TYPE: PRT
<213> ORGANISM: Homo sapiens

<400> SEQUENCE: 133

Asn Pro Leu Leu Lys His Tyr Arg Gly Pro Ala Gly Asp Ala
1               5                   10

<210> SEQ ID NO 134
<211> LENGTH: 15
<212> TYPE: PRT
<213> ORGANISM: Homo sapiens

<400> SEQUENCE: 134

Asn Pro Leu Leu Lys His Tyr Arg Gly Pro Ala Gly Asp Ala Thr
1               5                   10                  15

<210> SEQ ID NO 135
<211> LENGTH: 9
<212> TYPE: PRT
<213> ORGANISM: Homo sapiens

<400> SEQUENCE: 135

Pro Glu Leu Gly Pro Leu Pro Ala Leu
1               5

<210> SEQ ID NO 136
<211> LENGTH: 10
<212> TYPE: PRT
<213> ORGANISM: Homo sapiens

<400> SEQUENCE: 136

Pro Thr Glu Asn Phe Ser Leu Pro Val Leu
1               5                   10

<210> SEQ ID NO 137
<211> LENGTH: 13
<212> TYPE: PRT
<213> ORGANISM: Homo sapiens

<400> SEQUENCE: 137

Pro Val Leu Leu Ser Tyr Ile Gly Pro Ser Val Asn Lys
1               5                   10

<210> SEQ ID NO 138
<211> LENGTH: 9
<212> TYPE: PRT
<213> ORGANISM: Homo sapiens

<400> SEQUENCE: 138

Gln His Tyr Gln Gln Gln Gln Gln Val
1               5

<210> SEQ ID NO 139
<211> LENGTH: 10
<212> TYPE: PRT
<213> ORGANISM: Homo sapiens

<400> SEQUENCE: 139

Arg Ala Lys Asp Val Ile Ile Pro Ala Lys
1               5                   10

<210> SEQ ID NO 140
<211> LENGTH: 10
<212> TYPE: PRT
<213> ORGANISM: Homo sapiens

<400> SEQUENCE: 140

Arg Ala Leu Asp Val Asp Ser Gly Pro Leu
1               5                   10

<210> SEQ ID NO 141
<211> LENGTH: 9
<212> TYPE: PRT
<213> ORGANISM: Homo sapiens

<400> SEQUENCE: 141

Arg Glu Glu Gly Thr Pro Leu Thr Leu
1               5

<210> SEQ ID NO 142
<211> LENGTH: 9

```
<212> TYPE: PRT
<213> ORGANISM: Homo sapiens

<400> SEQUENCE: 142

Arg Lys Asp Glu Asp Arg Lys Gln Phe
1               5

<210> SEQ ID NO 143
<211> LENGTH: 9
<212> TYPE: PRT
<213> ORGANISM: Homo sapiens

<400> SEQUENCE: 143

Arg Lys Leu Ala Tyr Arg Pro Pro Lys
1               5

<210> SEQ ID NO 144
<211> LENGTH: 10
<212> TYPE: PRT
<213> ORGANISM: Homo sapiens

<400> SEQUENCE: 144

Arg Leu Gly Pro Pro Lys Arg Pro Pro Arg
1               5                   10

<210> SEQ ID NO 145
<211> LENGTH: 10
<212> TYPE: PRT
<213> ORGANISM: Homo sapiens

<400> SEQUENCE: 145

Arg Leu Lys Pro Phe Tyr Leu Val Pro Lys
1               5                   10

<210> SEQ ID NO 146
<211> LENGTH: 9
<212> TYPE: PRT
<213> ORGANISM: Homo sapiens

<400> SEQUENCE: 146

Arg Leu Gln Ser Lys Val Thr Ala Lys
1               5

<210> SEQ ID NO 147
<211> LENGTH: 9
<212> TYPE: PRT
<213> ORGANISM: Homo sapiens

<400> SEQUENCE: 147

Arg Pro Phe His Gly Trp Thr Ser Leu
1               5

<210> SEQ ID NO 148
<211> LENGTH: 9
<212> TYPE: PRT
<213> ORGANISM: Homo sapiens

<400> SEQUENCE: 148

Arg Pro Gly Pro Pro Thr Arg Pro Leu
1               5

<210> SEQ ID NO 149
<211> LENGTH: 8
<212> TYPE: PRT
<213> ORGANISM: Homo sapiens
```

<400> SEQUENCE: 149

Arg Pro His Gly Gly Lys Ser Leu
1               5

<210> SEQ ID NO 150
<211> LENGTH: 9
<212> TYPE: PRT
<213> ORGANISM: Homo sapiens

<400> SEQUENCE: 150

Arg Pro Lys Ala Gln Pro Thr Thr Leu
1               5

<210> SEQ ID NO 151
<211> LENGTH: 9
<212> TYPE: PRT
<213> ORGANISM: Homo sapiens

<400> SEQUENCE: 151

Arg Pro Gln Leu Lys Gly Val Val Leu
1               5

<210> SEQ ID NO 152
<211> LENGTH: 8
<212> TYPE: PRT
<213> ORGANISM: Homo sapiens

<400> SEQUENCE: 152

Arg Pro Arg Ala Pro Gly Pro Gln
1               5

<210> SEQ ID NO 153
<211> LENGTH: 10
<212> TYPE: PRT
<213> ORGANISM: Homo sapiens

<400> SEQUENCE: 153

Arg Pro Arg Lys Ala Phe Leu Leu Leu Leu
1               5                   10

<210> SEQ ID NO 154
<211> LENGTH: 9
<212> TYPE: PRT
<213> ORGANISM: Homo sapiens

<400> SEQUENCE: 154

Arg Pro Arg Pro Pro Val Leu Ser Val
1               5

<210> SEQ ID NO 155
<211> LENGTH: 9
<212> TYPE: PRT
<213> ORGANISM: Homo sapiens

<400> SEQUENCE: 155

Arg Gln Phe Trp Thr Arg Thr Lys Lys
1               5

<210> SEQ ID NO 156
<211> LENGTH: 9
<212> TYPE: PRT
<213> ORGANISM: Homo sapiens

<400> SEQUENCE: 156

Arg Gln Tyr Pro Glu Val Ile Lys Tyr
1               5

<210> SEQ ID NO 157
<211> LENGTH: 9
<212> TYPE: PRT
<213> ORGANISM: Homo sapiens

<400> SEQUENCE: 157

Arg Val Ala Lys Thr Asn Ser Leu Arg
1               5

<210> SEQ ID NO 158
<211> LENGTH: 9
<212> TYPE: PRT
<213> ORGANISM: Homo sapiens

<400> SEQUENCE: 158

Arg Val Phe Pro Tyr Ser Val Phe Tyr
1               5

<210> SEQ ID NO 159
<211> LENGTH: 10
<212> TYPE: PRT
<213> ORGANISM: Homo sapiens

<400> SEQUENCE: 159

Arg Val Asn Lys Val Ile Ile Gly Thr Lys
1               5                   10

<210> SEQ ID NO 160
<211> LENGTH: 9
<212> TYPE: PRT
<213> ORGANISM: Homo sapiens

<400> SEQUENCE: 160

Arg Tyr Phe Lys Gly Pro Glu Leu Leu
1               5

<210> SEQ ID NO 161
<211> LENGTH: 9
<212> TYPE: PRT
<213> ORGANISM: Homo sapiens

<400> SEQUENCE: 161

Arg Tyr Leu Asp Leu Phe Thr Ser Phe
1               5

<210> SEQ ID NO 162
<211> LENGTH: 8
<212> TYPE: PRT
<213> ORGANISM: Homo sapiens

<400> SEQUENCE: 162

Arg Tyr Asn Pro Tyr Leu Lys Arg
1               5

<210> SEQ ID NO 163
<211> LENGTH: 9
<212> TYPE: PRT
<213> ORGANISM: Homo sapiens

<400> SEQUENCE: 163

Arg Tyr Ser Pro Val Leu Ser Arg Phe

<210> SEQ ID NO 164
<211> LENGTH: 9
<212> TYPE: PRT
<213> ORGANISM: Homo sapiens

<400> SEQUENCE: 164

Arg Tyr Ser Thr Gln Ile His Ser Phe
1               5

<210> SEQ ID NO 165
<211> LENGTH: 9
<212> TYPE: PRT
<213> ORGANISM: Homo sapiens

<400> SEQUENCE: 165

Ser Glu Phe Asp Phe Phe Glu Arg Leu
1               5

<210> SEQ ID NO 166
<211> LENGTH: 9
<212> TYPE: PRT
<213> ORGANISM: Homo sapiens

<400> SEQUENCE: 166

Ser Glu Leu Val Tyr Thr Asp Val Leu
1               5

<210> SEQ ID NO 167
<211> LENGTH: 9
<212> TYPE: PRT
<213> ORGANISM: Homo sapiens

<400> SEQUENCE: 167

Ser Glu Ser Leu Pro Val Arg Thr Leu
1               5

<210> SEQ ID NO 168
<211> LENGTH: 10
<212> TYPE: PRT
<213> ORGANISM: Homo sapiens

<400> SEQUENCE: 168

Ser Phe Asp Asp Ala Phe Lys Ala Asp Ser
1               5                   10

<210> SEQ ID NO 169
<211> LENGTH: 10
<212> TYPE: PRT
<213> ORGANISM: Homo sapiens

<400> SEQUENCE: 169

Ser Phe Leu Asp Leu Ala Arg Asn Ile Phe
1               5                   10

<210> SEQ ID NO 170
<211> LENGTH: 9
<212> TYPE: PRT
<213> ORGANISM: Homo sapiens

<400> SEQUENCE: 170

Ser His Ile Thr Arg Ala Phe Thr Val
1               5

```
<210> SEQ ID NO 171
<211> LENGTH: 9
<212> TYPE: PRT
<213> ORGANISM: Homo sapiens

<400> SEQUENCE: 171

Ser His Ser His Val Gly Tyr Thr Leu
1               5

<210> SEQ ID NO 172
<211> LENGTH: 9
<212> TYPE: PRT
<213> ORGANISM: Homo sapiens

<400> SEQUENCE: 172

Ser His Thr Pro Trp Ile Val Ile Ile
1               5

<210> SEQ ID NO 173
<211> LENGTH: 10
<212> TYPE: PRT
<213> ORGANISM: Homo sapiens

<400> SEQUENCE: 173

Ser Ile Arg Arg Gly Phe Gln Val Tyr Lys
1               5                   10

<210> SEQ ID NO 174
<211> LENGTH: 11
<212> TYPE: PRT
<213> ORGANISM: Homo sapiens

<400> SEQUENCE: 174

Ser Ile Tyr Arg Gly Pro Ser His Thr Tyr Lys
1               5                   10

<210> SEQ ID NO 175
<211> LENGTH: 9
<212> TYPE: PRT
<213> ORGANISM: Homo sapiens

<400> SEQUENCE: 175

Ser Lys Asp Glu Ala Arg Ser Ser Phe
1               5

<210> SEQ ID NO 176
<211> LENGTH: 15
<212> TYPE: PRT
<213> ORGANISM: Homo sapiens

<400> SEQUENCE: 176

Ser Leu Gly Gly Lys Ala Thr Thr Ala Ser Gln Ala Lys Ala Val
1               5                   10                  15

<210> SEQ ID NO 177
<211> LENGTH: 10
<212> TYPE: PRT
<213> ORGANISM: Homo sapiens

<400> SEQUENCE: 177

Ser Leu Leu Glu Gln Gly Leu Val Glu Ala
1               5                   10

<210> SEQ ID NO 178
```

```
<211> LENGTH: 11
<212> TYPE: PRT
<213> ORGANISM: Homo sapiens

<400> SEQUENCE: 178

Ser Met Asn Val Gln Gly Asp Tyr Glu Pro Thr
1               5                   10

<210> SEQ ID NO 179
<211> LENGTH: 9
<212> TYPE: PRT
<213> ORGANISM: Homo sapiens

<400> SEQUENCE: 179

Ser Pro Ala His Pro Lys Gln Thr Leu
1               5

<210> SEQ ID NO 180
<211> LENGTH: 9
<212> TYPE: PRT
<213> ORGANISM: Homo sapiens

<400> SEQUENCE: 180

Ser Pro Ala Leu Lys Arg Leu Asp Leu
1               5

<210> SEQ ID NO 181
<211> LENGTH: 9
<212> TYPE: PRT
<213> ORGANISM: Homo sapiens

<400> SEQUENCE: 181

Ser Pro Ala Leu Pro Gly Leu Lys Leu
1               5

<210> SEQ ID NO 182
<211> LENGTH: 9
<212> TYPE: PRT
<213> ORGANISM: Homo sapiens

<400> SEQUENCE: 182

Ser Pro Lys Ser Asn Asp Ser Asp Leu
1               5

<210> SEQ ID NO 183
<211> LENGTH: 10
<212> TYPE: PRT
<213> ORGANISM: Homo sapiens

<400> SEQUENCE: 183

Ser Pro Met Pro Gly Thr Leu Thr Ala Leu
1               5                   10

<210> SEQ ID NO 184
<211> LENGTH: 9
<212> TYPE: PRT
<213> ORGANISM: Homo sapiens

<400> SEQUENCE: 184

Ser Pro Pro Pro Pro Pro Pro Pro
1               5

<210> SEQ ID NO 185
<211> LENGTH: 9
<212> TYPE: PRT
```

<213> ORGANISM: Homo sapiens

<400> SEQUENCE: 185

Ser Pro Gln Ala Glu Thr Arg Glu Ala
1               5

<210> SEQ ID NO 186
<211> LENGTH: 9
<212> TYPE: PRT
<213> ORGANISM: Homo sapiens

<400> SEQUENCE: 186

Ser Pro Arg Leu Ser Leu Leu Tyr Leu
1               5

<210> SEQ ID NO 187
<211> LENGTH: 9
<212> TYPE: PRT
<213> ORGANISM: Homo sapiens

<400> SEQUENCE: 187

Ser Pro Arg Gln Ala Leu Thr Asp Phe
1               5

<210> SEQ ID NO 188
<211> LENGTH: 8
<212> TYPE: PRT
<213> ORGANISM: Homo sapiens

<400> SEQUENCE: 188

Ser Pro Thr Lys Leu Pro Ser Ile
1               5

<210> SEQ ID NO 189
<211> LENGTH: 9
<212> TYPE: PRT
<213> ORGANISM: Homo sapiens

<400> SEQUENCE: 189

Ser Pro Tyr Leu Arg Pro Leu Thr Leu
1               5

<210> SEQ ID NO 190
<211> LENGTH: 9
<212> TYPE: PRT
<213> ORGANISM: Homo sapiens

<400> SEQUENCE: 190

Ser Arg Gly Asp Phe Val Val Glu Tyr
1               5

<210> SEQ ID NO 191
<211> LENGTH: 9
<212> TYPE: PRT
<213> ORGANISM: Homo sapiens

<400> SEQUENCE: 191

Ser Val Tyr Ser Pro Val Lys Lys Lys
1               5

<210> SEQ ID NO 192
<211> LENGTH: 9
<212> TYPE: PRT
<213> ORGANISM: Homo sapiens

```
<400> SEQUENCE: 192

Ser Tyr Leu Asn Ser Val Gln Arg Leu
1               5

<210> SEQ ID NO 193
<211> LENGTH: 9
<212> TYPE: PRT
<213> ORGANISM: Homo sapiens

<400> SEQUENCE: 193

Thr Ala Ser Pro Leu Val Lys Ser Val
1               5

<210> SEQ ID NO 194
<211> LENGTH: 9
<212> TYPE: PRT
<213> ORGANISM: Homo sapiens

<400> SEQUENCE: 194

Thr Glu Ala Gln Pro Gln Gly His Leu
1               5

<210> SEQ ID NO 195
<211> LENGTH: 9
<212> TYPE: PRT
<213> ORGANISM: Homo sapiens

<400> SEQUENCE: 195

Thr Glu Val Ile Phe Lys Val Ala Leu
1               5

<210> SEQ ID NO 196
<211> LENGTH: 9
<212> TYPE: PRT
<213> ORGANISM: Homo sapiens

<400> SEQUENCE: 196

Thr Phe Leu Pro Phe Ile His Thr Ile
1               5

<210> SEQ ID NO 197
<211> LENGTH: 11
<212> TYPE: PRT
<213> ORGANISM: Homo sapiens

<400> SEQUENCE: 197

Thr His Ala Ala Glu Asp Ile Val Tyr Thr Leu
1               5                   10

<210> SEQ ID NO 198
<211> LENGTH: 9
<212> TYPE: PRT
<213> ORGANISM: Homo sapiens

<400> SEQUENCE: 198

Thr Lys Phe Gly Gly Ile Val Val Leu
1               5

<210> SEQ ID NO 199
<211> LENGTH: 10
<212> TYPE: PRT
<213> ORGANISM: Homo sapiens

<400> SEQUENCE: 199
```

```
Thr Leu Lys Ser Gly Asp Gly Ile Thr Phe
1               5                   10

<210> SEQ ID NO 200
<211> LENGTH: 9
<212> TYPE: PRT
<213> ORGANISM: Homo sapiens

<400> SEQUENCE: 200

Thr Pro Ala Val Gly Arg Leu Glu Val
1               5

<210> SEQ ID NO 201
<211> LENGTH: 9
<212> TYPE: PRT
<213> ORGANISM: Homo sapiens

<400> SEQUENCE: 201

Thr Pro Glu Gln Gln Ala Ala Ile Leu
1               5

<210> SEQ ID NO 202
<211> LENGTH: 9
<212> TYPE: PRT
<213> ORGANISM: Homo sapiens

<400> SEQUENCE: 202

Thr Pro Ser Ser Arg Pro Ala Ser Leu
1               5

<210> SEQ ID NO 203
<211> LENGTH: 9
<212> TYPE: PRT
<213> ORGANISM: Homo sapiens

<400> SEQUENCE: 203

Thr Arg Ile Gly Leu Ala Pro Val Leu
1               5

<210> SEQ ID NO 204
<211> LENGTH: 9
<212> TYPE: PRT
<213> ORGANISM: Homo sapiens

<400> SEQUENCE: 204

Thr Val Lys Ala Thr Gly Pro Ala Leu
1               5

<210> SEQ ID NO 205
<211> LENGTH: 10
<212> TYPE: PRT
<213> ORGANISM: Homo sapiens

<400> SEQUENCE: 205

Val Ala Ala Leu Ala Ala His Thr Thr Phe
1               5                   10

<210> SEQ ID NO 206
<211> LENGTH: 9
<212> TYPE: PRT
<213> ORGANISM: Homo sapiens

<400> SEQUENCE: 206

Val Asp Asn Ile Phe Ile Leu Val Gln
1               5
```

<210> SEQ ID NO 207
<211> LENGTH: 10
<212> TYPE: PRT
<213> ORGANISM: Homo sapiens

<400> SEQUENCE: 207

Val Phe Asp Val Leu Asp Gly Glu Glu Met
1               5                   10

<210> SEQ ID NO 208
<211> LENGTH: 13
<212> TYPE: PRT
<213> ORGANISM: Homo sapiens

<400> SEQUENCE: 208

Val Gly Gly Leu Ser Phe Leu Val Asn His Asp Phe Ser
1               5                   10

<210> SEQ ID NO 209
<211> LENGTH: 9
<212> TYPE: PRT
<213> ORGANISM: Homo sapiens

<400> SEQUENCE: 209

Val Pro Ala Glu Gly Val Arg Thr Ala
1               5

<210> SEQ ID NO 210
<211> LENGTH: 10
<212> TYPE: PRT
<213> ORGANISM: Homo sapiens

<400> SEQUENCE: 210

Val Pro Leu Pro Pro Lys Gly Arg Val Leu
1               5                   10

<210> SEQ ID NO 211
<211> LENGTH: 11
<212> TYPE: PRT
<213> ORGANISM: Homo sapiens

<400> SEQUENCE: 211

Val Pro Leu Thr Arg Val Ser Gly Gly Ala Ala
1               5                   10

<210> SEQ ID NO 212
<211> LENGTH: 14
<212> TYPE: PRT
<213> ORGANISM: Homo sapiens

<400> SEQUENCE: 212

Val Pro Val Gly Gly Leu Ser Phe Leu Val Asn His Asp Phe
1               5                   10

<210> SEQ ID NO 213
<211> LENGTH: 15
<212> TYPE: PRT
<213> ORGANISM: Homo sapiens

<400> SEQUENCE: 213

Val Pro Val Gly Gly Leu Ser Phe Leu Val Asn His Asp Phe Ser
1               5                   10                  15

```
<210> SEQ ID NO 214
<211> LENGTH: 16
<212> TYPE: PRT
<213> ORGANISM: Homo sapiens

<400> SEQUENCE: 214

Val Pro Val Gly Gly Leu Ser Phe Leu Val Asn His Asp Phe Ser Pro
1               5                   10                  15

<210> SEQ ID NO 215
<211> LENGTH: 17
<212> TYPE: PRT
<213> ORGANISM: Homo sapiens

<400> SEQUENCE: 215

Val Pro Val Gly Gly Leu Ser Phe Leu Val Asn His Asp Phe Ser Pro
1               5                   10                  15

Leu

<210> SEQ ID NO 216
<211> LENGTH: 18
<212> TYPE: PRT
<213> ORGANISM: Homo sapiens

<400> SEQUENCE: 216

Val Pro Val Gly Gly Leu Ser Phe Leu Val Asn His Asp Phe Ser Pro
1               5                   10                  15

Leu Glu

<210> SEQ ID NO 217
<211> LENGTH: 9
<212> TYPE: PRT
<213> ORGANISM: Homo sapiens

<400> SEQUENCE: 217

Val Thr Asp Gly Lys Glu Val Leu Leu
1               5

<210> SEQ ID NO 218
<211> LENGTH: 11
<212> TYPE: PRT
<213> ORGANISM: Homo sapiens

<400> SEQUENCE: 218

Tyr His Ala Pro Pro Leu Ser Ala Ile Thr Phe
1               5                   10

<210> SEQ ID NO 219
<211> LENGTH: 9
<212> TYPE: PRT
<213> ORGANISM: Homo sapiens

<400> SEQUENCE: 219

Tyr Ile Leu Asp Pro Lys Gln Ala Leu
1               5

<210> SEQ ID NO 220
<211> LENGTH: 9
<212> TYPE: PRT
<213> ORGANISM: Homo sapiens

<400> SEQUENCE: 220

Tyr Leu Phe Ala Val Asn Ile Lys Leu
1               5
```

<210> SEQ ID NO 221
<211> LENGTH: 9
<212> TYPE: PRT
<213> ORGANISM: Homo sapiens

<400> SEQUENCE: 221

Tyr Leu Tyr Ile Thr Lys Val Leu Lys
1               5

<210> SEQ ID NO 222
<211> LENGTH: 9
<212> TYPE: PRT
<213> ORGANISM: Homo sapiens

<400> SEQUENCE: 222

Tyr Pro Asp Ser Lys Asp Leu Thr Met
1               5

<210> SEQ ID NO 223
<211> LENGTH: 14
<212> TYPE: PRT
<213> ORGANISM: Homo sapiens

<400> SEQUENCE: 223

Tyr Pro Thr Ile Lys Ile Leu Lys Lys Gly Gln Ala Val Asp
1               5                   10

<210> SEQ ID NO 224
<211> LENGTH: 15
<212> TYPE: PRT
<213> ORGANISM: Homo sapiens

<400> SEQUENCE: 224

Tyr Pro Thr Ile Lys Ile Leu Lys Lys Gly Gln Ala Val Asp Tyr
1               5                   10                  15

<210> SEQ ID NO 225
<211> LENGTH: 16
<212> TYPE: PRT
<213> ORGANISM: Homo sapiens

<400> SEQUENCE: 225

Tyr Pro Thr Ile Lys Ile Leu Lys Lys Gly Gln Ala Val Asp Tyr Glu
1               5                   10                  15

<210> SEQ ID NO 226
<211> LENGTH: 9
<212> TYPE: PRT
<213> ORGANISM: Homo sapiens

<400> SEQUENCE: 226

Tyr Pro Val Phe Arg Ile Leu Thr Leu
1               5

<210> SEQ ID NO 227
<211> LENGTH: 9
<212> TYPE: PRT
<213> ORGANISM: Homo sapiens

<400> SEQUENCE: 227

Tyr Val Phe Pro Gly Val Thr Arg Leu
1               5

```
<210> SEQ ID NO 228
<211> LENGTH: 9
<212> TYPE: PRT
<213> ORGANISM: Homo sapiens

<400> SEQUENCE: 228

Tyr Tyr Leu Asn Glu Ile Gln Ser Phe
1               5

<210> SEQ ID NO 229
<211> LENGTH: 9
<212> TYPE: PRT
<213> ORGANISM: Homo sapiens

<400> SEQUENCE: 229

Tyr Val Leu Asp His Leu Ile Val Val
1               5

<210> SEQ ID NO 230
<211> LENGTH: 9
<212> TYPE: PRT
<213> ORGANISM: Homo sapiens

<400> SEQUENCE: 230

Arg Pro Pro Ile Phe Ile Arg Arg Leu
1               5

<210> SEQ ID NO 231
<211> LENGTH: 9
<212> TYPE: PRT
<213> ORGANISM: Homo sapiens

<400> SEQUENCE: 231

Lys Leu Phe Glu Lys Val Lys Glu Val
1               5

<210> SEQ ID NO 232
<211> LENGTH: 9
<212> TYPE: PRT
<213> ORGANISM: Homo sapiens

<400> SEQUENCE: 232

Lys Pro Ser Glu Lys Ile Gln Val Leu
1               5

<210> SEQ ID NO 233
<211> LENGTH: 9
<212> TYPE: PRT
<213> ORGANISM: Homo sapiens

<400> SEQUENCE: 233

Arg Leu Arg Ala Glu Ala Gln Val Lys
1               5

<210> SEQ ID NO 234
<211> LENGTH: 8
<212> TYPE: PRT
<213> ORGANISM: Homo sapiens

<400> SEQUENCE: 234

Arg Ala Lys Phe Lys Gln Leu Leu
1               5

<210> SEQ ID NO 235
<211> LENGTH: 10
```

```
<212> TYPE: PRT
<213> ORGANISM: Homo sapiens

<400> SEQUENCE: 235

Ala Glu Gly Gly Val Gly Trp Arg His Trp
1               5                   10

<210> SEQ ID NO 236
<211> LENGTH: 9
<212> TYPE: PRT
<213> ORGANISM: Homo sapiens

<400> SEQUENCE: 236

Asn Leu Val Pro Met Val Ala Thr Val
1               5

<210> SEQ ID NO 237
<211> LENGTH: 13
<212> TYPE: PRT
<213> ORGANISM: Homo sapiens

<400> SEQUENCE: 237

Asn Ser Val Ile Ile Val Asp Lys Asn Gly Arg Leu Val
1               5                   10
```

CELL EPITOPES AND COMBINATION OF CELL EPITOPES FOR USE IN THE IMMUNOTHERAPY OF MYELOMA AND OTHER CANCERS

CROSS REFERENCE TO RELATED APPLICATIONS

This application is a Continuation Application of U.S. patent application Ser. No. 15/191,895, filed Jun. 24, 2016, issued as U.S. Pat. No. 10,196,422 which claims priority from GB 1511191.7 filed Jun. 25, 2015 and U.S. Provisional Application No. 62/184,500 filed Jun. 25, 2015. Each of these applications is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-049002_Sequence_Listing_ST25.txt" created on 16 Nov. 2018, and 38,243 bytes in size) is submitted concurrently with the instant application, and the entire contents of the Sequence Listing are incorporated herein by reference.

FIELD OF THE INVENTION

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I and II molecules of human tumor cells that can be used in vaccine compositions for eliciting anti-tumor immune responses, or as targets for the development of pharmaceutically/immunologically active compounds and cells.

BACKGROUND OF THE INVENTION

Multiple myeloma (MM), a low-grade B cell lymphoma, is characterized by the proliferation of malignant plasma cells in the bone marrow [14]. Despite recent advances in treatment, including high-dose chemotherapy followed by autologous stem cell transplantation, novel immunomodulatory drugs and proteasome inhibitors, MM remains largely incurable [15, 16]. This is mostly due to the persistence of minimal residual disease (MRD), which leads to high relapse rates [17, 18].

Considering the severe side-effects and expense associated with treating cancer, there is a need to identify factors that can be used in the treatment of cancer in general and myeloma in particular. There is also a need to identify factors representing biomarkers for cancer in general and myeloma in particular, leading to better diagnosis of cancer, assessment of prognosis, and prediction of treatment success.

Antigen-specific immunotherapy holds the potential to induce clinically effective anti-cancer T-cell responses and might be harnessed to guide and increase the specificity of cancer immunotherapy in future combination trials [3]. To this end, the exact knowledge of tumor-associated/specific T-cell epitopes is crucial. After decades of research into overexpressed tumor antigens, more recently the focus has shifted to the patient-individualized identification of mutation-derived neoantigens [4, 5]. The encouraging findings of these new studies [6-8] have led to neoepitopes being viewed as the dominant targets of anti-cancer immune responses [9-11].

However, analyzing the antigenome of hematological malignancies, the inventors have recently demonstrated that non-mutated antigens are relevant targets of spontaneous anti-leukemia T-cell responses [12, 13]. The strategy implemented in these studies differentially maps the naturally presented HLA ligandomes of hematological cells in health and disease by mass spectrometry and was found to efficiently identify relevant tumor-associated antigens.

So far, the only established immunotherapeutic approach for MM is allogenic stem cell transplantation, which is associated with a high morbidity and mortality and remains an option for only a fraction of patients [19-21]. Antigen-specific T-cell based immunotherapy [22, 23]—especially in the constellation of MRD characterized by favorable effector to target ratios—might present an effective, low side effect option [24].

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anti-cancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed. Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell-(CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

An array of myeloma-associated T-cell antigens has been described in previous studies [25-35]. Most of these antigens were identified based on gene expression analysis and reverse immunology. Some of these antigens (WT1 [36, 37], RHAMM [38, 39], hTERT [40] and Survivin [40, 41]) have already found their way into clinical trials, showing promising results in terms of induction of specific T-cell responses as well as clinical responses in single patients. However, broad clinical effectiveness has not yet been achieved. These previous studies were restricted to very few HLA-allotypes and single antigens/epitopes [42], limiting both, the population of patients eligible for this therapeutic approach and the spectrum of inducible tumor-specific T-cell responses. Of note, recent studies demonstrated lacking degrees of tumor-association for several of these tumor antigens, both on the transcriptome level [43] and importantly also on the level of HLA restricted presentation [12, 13].

Kowalewski et al. (in: Kowalewski et al. Carfilzomib alters the HLA-presented peptidome of myeloma cells and impairs presentation of peptides with aromatic C-termini. Blood Cancer J. 2016 Apr. 8) disclose that multiple myeloma is an immunogenic disease, which might be effectively targeted by antigen-specific T-cell immunotherapy. The relative presentation levels of 4780 different HLA ligands were quantified in an in vitro model employing carfilzomib treatment of MM.1S and U266 myeloma cells, which revealed significant modulation of a substantial fraction of the HLA-presented peptidome. These findings implicate that carfilzomib mediates a direct, peptide motif-specific inhibitory effect on HLA ligand processing and presentation. As a substantial, and this may have broad implications for the implementation of antigen-specific treatment approaches in patients undergoing carfilzomib treatment.

Immunotherapy of cancer represents an option of specific targeting of cancer cells while minimizing side effects. Cancer immunotherapy makes use of the existence of tumor associated antigens. It is therefore an object of the present invention, to provide novel epitopes to be used in the immunotherapy of cancer, in particular of myeloma.

SUMMARY OF THE INVENTION

In a first aspect of the present invention, the present invention relates to a peptide comprising an amino acid sequence selected from the group consisting of SEQ ID NO: 1 to SEQ ID NO: 228 or a variant sequence thereof which is at least 77%, preferably at least 88%, homologous (preferably at least 77% or at least 88% identical) to SEQ ID NO: 1 to SEQ ID NO: 228, wherein said variant binds to MHC and/or induces T cells cross-reacting with said peptide, or a pharmaceutical acceptable salt thereof, wherein said peptide is not the underlying full-length polypeptide.

BRIEF DESCRIPTION OF THE DRAWINGS

FIGS. 1A-6B depict embodiments as described herein.

Figure 1A:
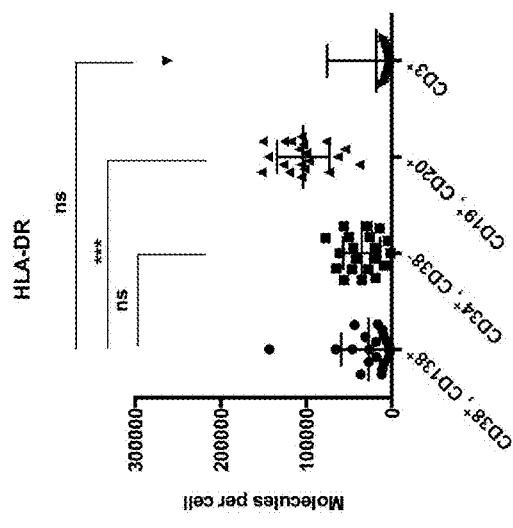

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

By analyzing the antigenic landscape of MM directly on the HLA ligand level the inventors here provide a panel of novel myeloma-associated epitopes suited for antigen-specific immunotherapy.

The present invention further relates to a peptide of the present invention comprising a sequence that is selected from the group consisting of SEQ ID NO: 1 to SEQ ID NO: 228 or a variant thereof, which is at least 77%, preferably at least 88%, homologous (preferably at least 77% or at least 88% identical) to SEQ ID NO: 1 to SEQ ID NO: 228, wherein said peptide or variant thereof has an overall length of between 8 and 100, preferably between 8 and 30, and most preferred of between 8 and 14 amino acids.

The following tables show the peptides according to the present invention, their respective SEQ ID NOs, the HLA binding, and the prospective source (underlying) genes for these peptides.

TABLE 1

Peptides according to the present invention

| SEQ ID No. | sequence | HLA | Gene name |
|---|---|---|---|
| 1 | AASPVVAEY | A*24 | LIME1 |
| 2 | AENAPSKEVL | B*40 | SLC1A5 |
| 3 | AEQEIARLVL | B*40:01 | CREB3 |
| 4 | AFIQAGIFQEF | A*23:01 | RAD1 |
| 5 | AHSEQLQAL | B*39 | TXNDC11 |
| 6 | AIILEAVNLPVDH | class II | SLC1A5 |
| 7 | AKRFDVSGY | B*15 | PDIA4 |
| 8 | ALDPLADKILI | A*02:01 | CRLS1 |
| 9 | ALKKPIKGK | A*03 | SETD8 |
| 10 | ALWGRTTLK | A*03 | DAP3 |
| 11 | APFQGDQRSL | B*07 | IRF9 |
| 12 | APKYGSYNVF | B*42:01 | MOGS |
| 13 | APRHPSTNSL | B*07 | NDUFAF4 |
| 14 | APRHPSTNSLL | B*07 | NDUFAF4 |
| 15 | APVGlmFLVAGKIV | class II | SLC1A5 |
| 16 | APVGlmFLVAGKIVE | class II | SLC1A5 |
| 17 | ASNPSNPRPSK | A*30:01 | WHSC1 1 |
| 18 | AVFIAQLSQQSLDF | class II | SLC1A5 |
| 19 | DALGAGILHHL | A*02 | SLC1A4 |
| 20 | DEVLLQKL | B*18 | PPP2R3C |
| 21 | DGDDVIIIGVFKGESDPAY | class II | PDIA4 |
| 22 | DIKDTDVlmKR | A*33 | MB21D1 |
| 23 | DIQDPGVPR | A*33 | SEMA4A |
| 24 | DLFRYNPYLKR | A*03 | NBN |
| 25 | DLLDGFIAR | A*03 | CRLS1 |
| 26 | DLNFPEIKR | A*03 | NOC2L |
| 27 | DLRPATDYHVR | A*33 | FNDC3B |
| 28 | DRYLLGTSL | B*27 | ASS1 |
| 29 | DSFERSNSL | A*68:02 | TBC1D4 |
| 30 | DTQSGSLLFIGR | A*03 | SERPINH1 |
| 31 | DVAEPYKVY | A*25 | IRF9 |
| 32 | DVNNIGKYR | A*03 | LAP3 |
| 33 | DVPDHIIAY | A*03 | KIAA1217 |
| 34 | EGNPLLKHYRGPAGDA | class II | SCL1A5 |
| 35 | EGNPLLKHYRGPAGDAT | class II | SLC1A5 |
| 36 | EIIEKNFDY | A*26 | TMEM126B |
| 37 | EIIEKNFDYLR | A*03 | TMEM126B |
| 38 | EITEVALEY | A*26 | TXNDC11 |
| 39 | ENGVLVLNDANFDNFV | class II | PDIA4 |
| 40 | EQLYDLTLEY | B*39 | NOC2L |
| 41 | ERFEKTFQL | B*39 | MOGS |
| 42 | EYGHIPSF | A*24:02 | ARHGAP11A |
| 43 | FAQIISVALI | A*02 | DOLK |
| 44 | FAYPAIRYL | A*02 | DAP3 |
| 45 | FFKPHWDEKF | A*24 | SERPINH1 |
| 46 | FISGHTSEL | A*02 | MOGS |
| 47 | FKSPAASSF | B*15 | NUPL2 |
| 48 | FLFQLLQLL | A*02 | SEMA4A |
| 49 | FLWDEGFHQL | A*02:01 | MOGS |
| 50 | FNFLRNVSL | B*08:01 | ARHGAP11A |
| 51 | FVFPGELLL | A*02:01 | SLC1A5 |
| 52 | GAKASTTSL | C*03:03 | CMTR1 |
| 53 | GELIEVVHL | B*40 | NUDT14 |
| 54 | GETAFAFHL | B*40:01 | SLX1A |
| 55 | GEVAPSMFL | B*40:01 | NPC1 |
| 56 | GEVQDLLVRL | B*40 | BAZ2B |
| 57 | GKVQENSAY | B*15 | NOC2L |
| 58 | GKYIFASIL | B*15 | SLC1A4 |
| 59 | GNPLLKHYRGPAGDA | class II | SLC1A5 |
| 60 | GPFSQFIKA | B*55 | FNDC3B |
| 61 | GPRPITQSEL | B*07 | UBL7 |
| 62 | GRYPGVSNY | B*27 | NAE1 |
| 63 | GYPTIKILKKGQAVDYE | class II | PDIA4 |
| 64 | GYPTIKILKKGQAVDYEG | class II | PDIA4 |
| 65 | HPKQPEPSA | B*42:01 | TXNDC11 |
| 66 | HPKQPEPSAT | B*42:01 | TXNDC11 |
| 67 | HSMDFVAYR | A*03 | CYC1 |
| 68 | IADPFFRSA | C*03:04 | BTN3A1 |
| 69 | IEHPSMSVY | B*18 | TP53INP1 |
| 70 | IESHPDNAL | B*40 | NAE1 NEDD8 |
| 71 | IEVEAVRF | B*18 | KIAA1217 |
| 72 | IHILDVLVL | B*15 | CMTR1 |
| 73 | IIFDRPLLY | A*03 | DOLK |
| 74 | ILRDGITAGK | A*03:01 | BTN3A1 |
| 75 | ILWETVPSM | A*02:01 | FNDC3B |

TABLE 1-continued

Peptides according to the present invention

| SEQ ID No. | sequence | HLA | Gene name |
|---|---|---|---|
| 76 | IPAKPPVSF | B*07:02, B*42:01 | TXNDC11 |
| 77 | IPAKPPVSFF | B*07:02 | TXNDC11 |
| 78 | IQAGIFQEF | B*15 | RAD1 |
| 79 | IQILHQVL | B*15 | NPC1 |
| 80 | IVDRTTTVVNVEG | class II | SLC1A4 |
| 81 | IVDRTTTVVNVEGDA | class II | SLC1A4 |
| 82 | KAMEAASSL | A*02 | WHSC1 |
| 83 | KAVNPGRSL | A*02 | BFAR |
| 84 | KDARKGPLVP | B*07 | SETD8 |
| 85 | KEENGVLVL | B*40 | PDIA4 |
| 86 | KEFAAIVDV | B*40 | TXNDC11 |
| 87 | KEGLILPETL | B*40:01 | CREB3 |
| 88 | KILKPVKKK | A*03 | CSNK2A1 |
| 89 | KLGWLSSMTK | A*03 | COG1 |
| 90 | KLPLPLPPRL | B*07 | HSH2D |
| 91 | KLRELTQRY | A*03 | SPATC1L |
| 92 | KLSSLIILM | A*02:01 | SERPINH1 |
| 93 | KPKDPLKISL | B*07 | PPP2R3C |
| 94 | KPQPRPQTL | B*07 | DYRK4 |
| 95 | KPRPPQGL | B*07:02, B*42:01 | MOGS |
| 96 | KPRPPQGLVR | B*07 | MOGS |
| 97 | KPSTKALVL | B*07 | RAD1 |
| 98 | KPYPNSEAARA | B*55 | CYC1 |
| 99 | KQHGIPIPV | B*27 | ASS1 |
| 100 | KTEVHIRPK | A*03:01 | LAP3 |
| 101 | KTQLLPTSK | A*33 | ARHGAP11A |
| 102 | KVMLSALGML | A*02 | CYC1 |
| 103 | KYESIRLLF | A*24 | SNX14 14 |
| 104 | KYPDSHLPTL | A*24 | KIAA1217 |
| 105 | LAALPGVSL | A*02 | LIME1 |
| 106 | LADHTVHVL | A*02:01 | ARHGAP11A |
| 107 | LAFPGEMLL | A*02 | SLC1A4 |
| 108 | LAHVGPRL | A*02:01 | SLX1A |
| 109 | LEKEGLIL | B*40 | CREB3 |
| 110 | LKIPISIEF | B*15 | MOGS |
| 111 | LLFPYILPPK | A*02 | SNX14 |
| 112 | LLRFSQDNA | A*02:01 | LAP3 |
| 113 | LPAEHGVL | B*07 | CREB3 |
| 114 | LPKDVSPTQA | B*55 | COG1 |
| 115 | LPPPPHVPL | B*07:02 | SLX1A |
| 116 | LPQLHSLVL | B*07 | LRRC47 |
| 117 | LPVLLSYIGPSVNK | class II | NPC1 |
| 118 | LRFSQDNA | C*07 | LAP3 |
| 119 | LYDVAGQGYL | B*24:02 | PPP2R3C |
| 120 | MDLQPGNALKR | n.a. | LRRC47 |
| 121 | MHGQPSPSL | B*15 | TMEM126B |
| 122 | mNIFRLTGDLSH | class II | KDELR2 |
| 123 | mPDDSYmVDYFKSISQ | class II | NPC1 |
| 124 | mPDDSYmVDYFKSISQY | class II | NPC1 |
| 125 | MRLSLPLLL | B*27 | MZB1 |
| 126 | MRLSLPLLLL | B*27 | MZB1 |
| 127 | NEDFSFHY | B*18 | P49770 EIF2B2 |
| 128 | NEFPVFDEF | B*18:01 | MB21D1 |
| 129 | NEVIMTIGF | B*18:01 | P49770 EIF2B2 |
| 130 | NGVLVLNDANFDNFV | class II | PDIA4 |
| 131 | NIGQKEDFEEA | A*02 | ASS1 |
| 132 | NMDLMRADM | A*02 | LAP3 |
| 133 | NPLLKHYRGPAGDA | class II | SLC1A5 |
| 134 | NPLLKHYRGPAGDAT | class II | SLC1A5 |
| 135 | PELGPLPAL | B*18, B*40 | LRRC47 |
| 136 | PTENFSLPVL | A*02 | ZBTB21 |
| 137 | PVLLSYIGPSVNK | class II | NPC1 |
| 138 | QHYQQQQQV | B*15:10 | BHLHA15 |
| 139 | RAKDVIIPAK | A*03 | TXNDC11 |
| 140 | RALDVDSGPL | A*02 | LIME1 |
| 141 | REEGTPLTL | B*40:01 | NOC2L |
| 142 | RKDEDRKQF | B*15 | NOC2L |
| 143 | RKLAYRPPK | B*15 | CYC1 |
| 144 | RLGPPKRPPR | A*30 | MRPS12 |
| 145 | RLKPFYLVPK | A*03 | MB21D1 |
| 146 | RLQSKVTAK | A*03 | ASS1 |
| 147 | RPFHGVVTSL | B*07:02 | MOGS |
| 148 | RPGPPTRPL | B*07:02 | FNDC3B |
| 149 | FPHGGKSL | B*07, B*42:01 | TXNDC11 |

TABLE 1-continued

Peptides according to the present invention

| SEQ ID No. | sequence | HLA | Gene name |
|---|---|---|---|
| 150 | RPKAQPTTL | B*07; B*42:01 | MED27 |
| 151 | RPQLKGVVL | B*07 | MRPS12 |
| 152 | RPRAPGPQ | B*07 | WFS1 |
| 153 | RPRKAFLLLL | B*07, B*42:01 | PDIA4 |
| 154 | RPRPPVLSV | B*07 | ZBTB21 |
| 155 | RQFVVTRTKK | A*03:01 | MRPL55 |
| 156 | RQYPEVIKY | B*39 | BAZ2B |
| 157 | RVAKTNSLR | A*03:01 | Q53HL2 CDCA8 |
| 158 | RVFPYSVFY | A*03:01 | NPC1 |
| 159 | RVNKVIIGTK | A*03:01 | P49770 EIF2B2 |
| 160 | RYFKGPELL | A*24 | CSNK2A1 |
| 161 | RYLDLFTSF | A*24:02 | KDELR2 |
| 162 | RYNPYLKR | A*33 | NBN |
| 163 | RYSPVLSRF | A*24:02 | COG1 |
| 164 | RYSTQIHSF | A*24:02 | BHLHA15 |
| 165 | SEFDFFERL | B*18:01, B*40 | SEMA4A |
| 166 | SELVYTDVL | B*40 | MZB1 |
| 167 | SESLPVRTL | B*40:01 | FNDC3B |
| 168 | SFDDAFKADS | n.a. | CMTR1 |
| 169 | SFLDLARNIF | A*24:02 | SLC1A5 |
| 170 | SHITRAFTV | B*15 | NPC1 |
| 171 | SHSHVGYTL | B*39 | HSH2D |
| 172 | SHTPWIVII | B*15 | NAE1 |
| 173 | SIRRGFQVYK | A*03 | CYC1 |
| 174 | SIYRGPSHTYK | A*03 | FNDC3B |
| 175 | SKDEARSSF | B*15 | ARHGAP11A |
| 176 | SLGGKATTASQAKAV | class II | SERPINH1 |
| 177 | SLLEQGLVEA | A*02 | WHSC1 |
| 178 | SMNVQGDYEPT | A*02 | ASS1 |
| 179 | SPAHPKQTL | B*07 | BAZ2B |
| 180 | SPALKRLDL | B*07:02 | COG1 |
| 181 | SPALPGLKL | B*07 | TNFRSF13B |
| 182 | SPKSNDSDL | B*42:01 | FNDC3B |
| 183 | SPMPGTLTAL | B*07 | RAD1 |
| 184 | SPPPPPPPP | B*07 | KIAA1217 |
| 185 | SPQAETREA | B*55 | NOC2L |
| 186 | SPRLSLLYL | B*07 | BFAR |
| 187 | SPRQALTDF | B*07:02 | COG1 |
| 188 | SPTKLPSI | B*55 | NBN |
| 189 | SPYLRPLTL | B*07:02 | NUDT14 |
| 190 | SRGDFVVEY | C*07 | SETD8 |
| 191 | SVYSPVKKK | A*03 | NUPL2 |
| 192 | SYLNSVQRL | A*24:02 | NUPL2 |
| 193 | TASPLVKSV | C*12 | ARHGAP11A |
| 194 | TEAQPQGHL | B*40 | BHLHA15 |
| 195 | TEVIFKVAL | B*18, B*40 | TBC1D4 |
| 196 | TFLPFIHTI | A*23:01 | BFAR |
| 197 | THAAEDIVYTL | B*39:01 | FNDC3B |
| 198 | TKFGGIVVL | B*15 | NPC1 |
| 199 | TLKSGDGITF | B*15 | NBN |
| 200 | TPAVGRLEV | B*07, B*42:01 | Q53HL2 |
| 201 | TPEQQAAIL | B*07 | IRF9 |
| 202 | TPSSRPASL | B*07 | UBL7 |
| 203 | TRIGLAPVL | B*15 | CRLS1 |
| 204 | TVKATGPAL | A*02 | MRPL55 |
| 205 | VAALAAHTTF | A*24 | TP53INP1 |
| 206 | VDNIFILVQ | n.a. | NPC1 |
| 207 | VFDVLDGEEM | A*24 | CMTR1 |
| 208 | VGGLSFLVNHDFS | class II | KDELR2 |
| 209 | VPAEGVRTA | B*55 | MOGS |
| 210 | VPLPPKGRVL | B*42:01 | TMEM126B |
| 211 | VPLTRVSGGAA | B*42:01 | SEMA4A |
| 212 | VPVGGLSFLVNHDF | class II | KDELR2 |
| 213 | VPVGGLSFLVNHDFS | class II | KDELR2 |
| 214 | VPVGGLSFLVNHDFSP | class II | KDELR2 |
| 215 | VPVGGLSFLVNHDFSPL | class II | KDELR2 |
| 216 | VPVGGLSFLVNHDFSPLE | class II | KDELR2 |
| 217 | VTDGKEVLL | A*02 | MOGS |
| 218 | YHAPPLSAITF | B*15 | ZBTB21 |
| 219 | YILDPKQAL | A*02 | TXNDC11 |
| 220 | YLFAVNIKL | A*02 | CMTR1 |
| 221 | YLYITKVLK | A*03:01 | KDELR2 |
| 222 | YPDSKDLTM | B*07 | DYRK4 |

TABLE 1-continued

Peptides according to the present invention

| SEQ ID No. | sequence | HLA | Gene name |
|---|---|---|---|
| 223 | YPTIKILKKGQAVD | class II | PDIA4 |
| 224 | YPTIKILKKGQAVDY | class II | PDIA4 |
| 225 | YPTIKILKKGQAVDYE | class II | PDIA4 |
| 226 | YPVFRILTL | B*07 | BTN3A1 |
| 227 | YVFPGVTRL | A*02 | SPATC1L |
| 228 | YYLNEIQSF | A*24 | SPATC1L |

The abbreviations are as follows: TXNDC11=thioredoxin domain containing 11, MOGS=mannosyl-oligosaccharide glucosidase, FNDC3B=fibronectin type III domain containing 3B, NUDT14=nudix (nucleoside diphosphate linked moiety X)-type motif 14, SLC1A5=solute carrier family 1 (neutral amino acid transporter), member 5, ARHGAP11A=Rho GTPase activating protein 11A, BHLHA15=basic helix-loop-helix family, member al 5, LRRC47=leucine rich repeat containing 47, PPP2R3C=protein phosphatase 2, regulatory subunit B", gamma, SLX1A=SLX1 structure-specific endonuclease subunit homolog A (S. cerevisiae), BAZ2B=bromodomain adjacent to zinc finger domain, 2B, NOC2L=nucleolar complex associated 2 homolog (S. cerevisiae), BTN3A1=butyrophilin, subfamily 3, member A1, TNFRSF13B=tumor necrosis factor receptor superfamily, member 13B, NPC1=Niemann-Pick disease, type C1, MRPS12=mitochondrial ribosomal protein S12, NUPL2=nucleoporin like 2, CREB3=cAMP responsive element binding protein 3, TBC1 D4=TBC1 domain family, member 4, RAD1=RAD1 checkpoint DNA exonuclease, NBN=nibrin, WFS1=Wolfram syndrome 1, WHSC1=Wolf-Hirschhorn syndrome candidate 1, ASS1=argininosuccinate synthase 1, CYC1=cytochrome c-1, PDIA4=protein disulfide isomerase family A, member 4, LAP3=leucine aminopeptidase 3, KDELR2=KDEL (LysAsp-Glu-Leu) endoplasmic reticulum protein retention receptor, SLC1A4=solute carrier family 1 (glutamate/neutral amino acid transporter), member 4, P49770=EIF2B2=eukaryotic translation initiation factor 2B, subunit 2 beta, 39 kDa, SERPINH1=serpin peptidase inhibitor, Glade H (heat shock protein 47), member 1, DAP3=death associated protein 3, IRF9=interferon regulatory factor 9, NAE1=NEDD8 activating enzyme E1 subunit 1, Q53HL2=CDCA8=cell division cycle associated 8, KIAA1217, MED27=mediator complex subunit 27, MRPL55=mitochondrial ribosomal protein L55, TMEM126B=transmembrane protein 126B, CMTR1=cap methyltransferase 1, MB21D1=Mab-21 domain containing 1, CSNK2A1=casein kinase 2, alpha 1 polypeptide, COG1=component of oligomeric golgi complex 1, MZB1=marginal zone B and B1 cell-specific protein, TP531NP1=tumor protein p53 inducible nuclear protein 1, HSH2D=hematopoietic SH2 domain containing, UBL7=ubiquitin-like 7, SPATC1L=spermatogenesis and centriole associated 1-like, SEMA4A=sema domain, immunoglobulin domain (Ig), transmembrane domain (TM) and short cytoplasmic domain, (semaphorin) 4A, LIME1=Lck interacting transmembrane adaptor 1, SETD8=SET domain containing (lysine methyltransferase) 8, DYRK4=dual-specificity tyrosine-(Y)phosphorylation regulated kinase 4, BFAR=bifunctional apoptosis regulator, NDUFAF4=NADH dehydrogenase (ubiquinone) complex I, assembly factor 4, ZBTB21=zinc finger and BTB domain containing 21, DOLK=dolichol kinase, SNX14=sorting nexin 14, NPC1=Niemann-Pick disease, type C1.

The present invention furthermore generally relates to the peptides according to the present invention for use in the treatment of proliferative diseases, such as, cancer, wherein said cancer is selected from the group of lung cancer, brain cancer, hepatic cancer, kidney cancer, colorectal cancer, liver cancer, pancreatic cancer, prostate cancer, leukemia, breast cancer, Merkel cell carcinoma, melanoma, ovarian cancer, stomach cancer, endometrial cancer, and esophageal cancer and other tumors that show an overexpression of a protein from which a peptide SEQ ID No. 1 to SEQ ID No. 228, and in particular myeloma.

Particularly preferred are the peptides—alone or in combination—according to the present invention selected from the group consisting of the SEQ ID NOs according to the following Table 2, and their uses in the immunotherapy of proliferative diseases, such as, cancer, wherein said cancer is selected from the group of lung cancer, brain cancer, hepatic cancer, kidney cancer, colorectal cancer, liver cancer, pancreatic cancer, prostate cancer, leukemia, breast cancer, Merkel cell carcinoma, melanoma, ovarian cancer, and esophageal cancer and other tumors that show an overexpression of a protein from which a peptide SEQ ID No. 1 to SEQ ID No. 228, and in particular myeloma.

TABLE 2

Preferred peptides of the invention

| SEQ ID No. | sequence | HLA | Gene name |
|---|---|---|---|
| 1 | AASPVVAEY | A*24 | LIME1 |
| 2 | AENAPSKEVL | B*40 | SLC1A5 |
| 4 | AFIQAGIFQEF | A*23:01 | RAD1 |
| 5 | AHSEQLQAL | B*39 | TXNDC11 |
| 6 | AIILEAVNLPVDH | class II | SLC1A5 |
| 7 | AKRFDVSGY | B*15 | PDIA4 |
| 12 | APKYGSYNVF | B*42:01 | MOGS |
| 15 | APVGlmFLVAGKIV | class II | SLC1A5 |
| 16 | APVGlmFLVAGKIVE | class II | SLC1A5 |
| 17 | ASNPSNPRPSK | A*30:01 | WHSC1 1 |
| 18 | AVFIAQLSQQSLDF | class II | SLC1A5 |
| 19 | DALGAGILHHL | A*02 | SLC1A4 |
| 20 | DEVLLQKL | B*18 | PPP2R3C |
| 21 | DGDDVIIIGVFKGESDPAY | class II | PDIA4 |
| 22 | DIKDTDVlmKR | A*33 | MB21D1 |
| 23 | DIQDPGVPR | A*33 | SEMA4A |
| 24 | DLFRYNPYLKR | A*03 | NBN |
| 25 | DLLDGFIAR | A*03 | CRLS1 |
| 26 | DLNFPEIKR | A*03 | NOC2L |
| 27 | DLRPATDYHVR | A*33 | FNDC3B |

TABLE 2-continued

Preferred peptides of the invention

| SEQ ID No. | sequence | HLA | Gene name |
|---|---|---|---|
| 28 | DRYLLGTSL | B*27 | ASS1 |
| 29 | DSFERSNSL | A*68:02 | TBC1D4 |
| 30 | DTQSGSLLFIGR | A*03 | SERPINH1 |
| 32 | DVNNIGKYR | A*03 | LAP3 |
| 33 | DVPDHIIAY | A*03 | KIAA1217 |
| 34 | EGNPLLKHYRGPAGDA | class II | SLC1A5 |
| 35 | EGNPLLKHYRGPAGDAT | class II | SLC1A5 |
| 37 | EIIEKNFDYLR | A*03 | TMEM126B |
| 38 | EITEVALEY | A*26 | TXNDC11 |
| 39 | ENGVLVLNDANFDNFV | class II | PDIA4 |
| 40 | EQLYDLTLEY | B*39 | NOC2L |
| 42 | EYGHIPSF | A*24:02 | ARHGAP11A |
| 46 | FISGHTSEL | A*02 | MOGS |
| 47 | FKSPAASSF | B*15 | NUPL2 |
| 48 | FLFQLLQLL | A*02 | SEMA4A |
| 50 | FNFLRNVSL | B*08:01 | ARHGAP11A |
| 52 | GAKASTTSL | C*03:03 | CMTR1 |
| 53 | GELIEVVHL | B*40 | NUDT14 |
| 54 | GETAFAFHL | B*40:01 | SLX1A |
| 55 | GEVAPSMFL | B*40:01 | NPC1 |
| 56 | GEVQDLLVRL | B*40 | BAZ2B |
| 57 | GKVQENSAY | B*15 | NOC2L |
| 58 | GKYIFASIL | B*15 | SLC1A4 |
| 59 | GNPLLKHYRGPAGDA | class II | SLC1A5 |
| 60 | GPFSQFIKA | B*55 | FNDC3B |
| 63 | GYPTIKILKKGQAVDYE | class II | PDIA4 |
| 64 | GYPTIKILKKGQAVDYEG | class II | PDIA4 |
| 65 | HPKQPEPSA | B*42:01 | TXNDC11 |
| 66 | HPKQPEPSAT | B*42:01 | TXNDC11 |
| 68 | IADPFFRSA | C*03:04 | BTN3A1 |
| 69 | IEHPSMSVY | B*18 | TP53INP1 |
| 72 | IHILDVLVL | B*15 | CMTR1 |
| 79 | IQILHQVL | B*15 | NPC1 |
| 80 | IVDRTTTVVNVEG | class II | SLC1A4 |
| 81 | IVDRTTTVVNVEGDA | class II | SLC1A4 |
| 84 | KDARKGPLVP | B*07 | SETD8 |
| 85 | KEENGVLVL | B*40 | PDIA4 |
| 86 | KEFAAIVDV | B*40 | TXNDC11 |
| 87 | KEGLILPETL | B*40:01 | CREB3 |
| 89 | KLGWLSSMTK | A*03 | COG1 |
| 94 | KPQPRPQTL | B*07 | DYRK4 |
| 96 | KPRPPQGLVR | B*07 | MOGS |
| 98 | KPYPNSEAARA | B*55 | CYC1 |
| 99 | KQHGIPIPV | B*27 | ASS1 |
| 101 | KTQLLPTSK | A*33 | ARHGAP11A |
| 102 | KVMLSALGML | A*02 | CYC1 |
| 104 | KYPDSHLPTL | A*24 | KIAA1217 |
| 106 | LADHTVHVL | A*02:01 | ARHGAP11A |
| 107 | LAFPGEMLL | A*02 | SLC1A4 |
| 108 | LAHVGPRL | A*02:01 | SLX1A |
| 109 | LEKEGLIL | B*40 | CREB3 |
| 110 | LKIPISIEF | B*15 | MOGS |
| 112 | LLRFSQDNA | A*02:01 | LAP3 |
| 113 | LPAEHGVL | B*07 | CREB3 |
| 114 | LPKDVSPTQA | B*55 | COG1 |
| 117 | LPVLLSYIGPSVNK | class II | NPC1 |
| 118 | LRFSQDNA | C*07 | LAP3 |
| 119 | LYDVAGQGYL | B*24:02 | PPP2R3C |
| 120 | MDLQPGNALKR | n.a. | LRRC47 |
| 122 | mNIFRLTGDLSH | class II | KDELR2 |
| 123 | mPDDSYmVDYFKSISQ | class II | NPC1 |
| 124 | mPDDSYmVDYFKSISQY | class II | NPC1 |
| 126 | MRLSLPLLLL | B*27 | MZB1 |
| 127 | NEDFSFHY | B*18 | P49770 EIF2B2 |
| 128 | NEFPVFDEF | B*18:01 | MB21D1 |
| 130 | NGVLVLNDANFDNFV | class II | PDIA4 |
| 131 | NIGQKEDFEEA | A*02 | ASS1 |
| 132 | NMDLMRADM | A*02 | LAP3 |
| 133 | NPLLKHYRGPAGDA | class II | SLC1A5 |
| 134 | NPLLKHYRGPAGDAT | class II | SLC1A5 |
| 136 | PTENFSLPVL | A*02 | ZBTB21 |
| 137 | PVLLSYIGPSVNK | class II | NPC1 |
| 138 | QHYQQQQQV | B*15:10 | BHLHA15 |
| 139 | RAKDVIIPAK | A*03 | TXNDC11 |
| 140 | RALDVDSGPL | A*02 | LIME1 |

TABLE 2-continued

Preferred peptides of the invention

| SEQ ID No. | sequence | HLA | Gene name |
|---|---|---|---|
| 142 | RKDEDRKQF | B*15 | NOC2L |
| 143 | RKLAYRPPK | B*15 | CYC1 |
| 145 | RLKPFYLVPK | A*03 | MB21D1 |
| 148 | RPGPPTRPL | B*07:02 | FNDC3B |
| 149 | RPHGGKSL | B*07, B*42:01 | TXNDC11 |
| 152 | RPRAPGPQ | B*07 | WFS1 |
| 158 | RVFPYSVFY | A*03:01 | NPC1 |
| 161 | RYLDLFTSF | A*24:02 | KDELR2 |
| 162 | RYNPYLKR | A*33 | NBN |
| 166 | SELVYTDVL | B*40 | MZB1 |
| 168 | SFDDAFKADS | n.a. | CMTR1 |
| 169 | SFLDLARNIF | A*24:02 | SLC1A5 |
| 170 | SHITRAFTV | B*15 | NPC1 |
| 172 | SHTPWIVII | B*15 | NAE1 |
| 175 | SKDEARSSF | B*15 | ARHGAP11A |
| 176 | SLGGKATTASQAKAV | class II | SERPINH1 |
| 178 | SMNVQGDYEPT | A*02 | ASS1 |
| 185 | SPQAETREA | B*55 | NOC2L |
| 188 | SPTKLPSI | B*55 | NBN |
| 193 | TASPLVKSV | C*12 | ARHGAP11A |
| 194 | TEAQPQGHL | B*40 | BHLHA15 |
| 196 | TFLPFIHTI | A*23:01 | BFAR |
| 197 | THAAEDIVYTL | B*39:01 | FNDC3B |
| 198 | TKFGGIVVL | B*15 | NPC1 |
| 203 | TRIGLAPVL | B*15 | CRLS1 |
| 204 | TVKATGPAL | A*02 | MRPL55 |
| 205 | VAALAAHTTF | A*24 | TP53INP1 |
| 206 | VDNIFILVQ | n.a. | NPC1 |
| 207 | VFDVLDGEEM | A*24 | CMTR1 |
| 208 | VGGLSFLVNHDFS | class II | KDELR2 |
| 209 | VPAEGVRTA | B*55 | MOGS |
| 210 | VPLPPKGRVL | B*42:01 | TMEM126B |
| 211 | VPLTRVSGGAA | B*42:01 | SEMA4A |
| 212 | VPVGGLSFLVNHDF | class II | KDELR2 |
| 213 | VPVGGLSFLVNHDFS | class II | KDELR2 |
| 214 | VPVGGLSFLVNHDFSP | class II | KDELR2 |
| 215 | VPVGGLSFLVNHDFSPL | class II | KDELR2 |
| 216 | VPVGGLSFLVNHDFSPLE | class II | KDELR2 |
| 218 | YHAPPLSAITF | B*15 | ZBTB21 |
| 219 | YILDPKQAL | A*02 | TXNDC11 |
| 222 | YPDSKDLTM | B*07 | DYRK4 |
| 223 | YPTIKILKKGQAVD | class II | PDIA4 |
| 224 | YPTIKILKKGQAVDY | class II | PDIA4 |
| 225 | YPTIKILKKGQAVDYE | class II | PDIA4 |

Many of the peptides according to the present invention are also found on other tumor types and can, thus, also be used in the immunotherapy of other indications.

Thus, another aspect of the present invention relates to the use of the peptides according to the present invention for the—preferably combined—treatment of a proliferative disease selected from the group of cancer, wherein said cancer is selected from the group of lung cancer, brain cancer, hepatic cancer, kidney cancer, colorectal cancer, liver cancer, pancreatic cancer, prostate cancer, leukemia, breast cancer, Merkel cell carcinoma, melanoma, ovarian cancer, and esophageal cancer and other tumors that show an overexpression of a protein from which a peptide SEQ ID No. 1 to SEQ ID No. 228, and in particular myeloma.

The present invention furthermore relates to peptides according to the present invention that have the ability to bind to a molecule of the human major histocompatibility complex (MHC) class-I or -II, or in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 228.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 228, preferably containing at least one SEQ ID No. according to table 2, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are lung cancer, brain cancer, hepatic cancer, kidney cancer, colorectal cancer, liver cancer, pancreatic cancer, prostate cancer, leukemia, breast cancer, Merkel cell carcinoma, melanoma, ovarian cancer, and esophageal cancer cells, and preferably myeloma cells.

The present invention further relates to biomarkers based on the peptides according to the present invention, herein called "targets" that can be used in the diagnosis of cancer, preferably myeloma. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or even longer, and in case of MHC class II peptides (e.g. elongated variants of the peptides of the invention) they can be as long as 15, 16, 17, 18, 19, 20 or 23 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 2A

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
| --- | --- | --- |
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein preferably bind to HLA-A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 228 or a variant thereof which is 88% homologous to SEQ ID NO: 1 to SEQ ID NO: 228, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 228. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 228, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 4.

TABLE 4

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |

TABLE 4-continued

Combinations of the elongations of peptides of the invention

| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 or 23 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 228.

"Consisting essentially of" shall mean that a peptide according to the present invention, in addition to the sequence according to any of SEQ ID NO: 1 to SEQ ID NO 228 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, Gen Bank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and the references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethan-edithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as recrystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from myeloma samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from myeloma patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from myeloma samples were purified and HLA-associated peptides were isolated and analyzed by LC-MS (see examples). All TUMAPs contained in the present application were identified with this approach on primary myeloma samples confirming their presentation on myeloma.

TUMAPs identified on multiple myeloma and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention provides peptides that are useful in treating cancers/tumors, preferably myeloma that over- or exclusively present the peptides of the invention. These peptides were shown by mass spectrometry to be naturally presented by HLA molecules on human myeloma samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy plasma cells or other normal tissue cells, demonstrating a high degree of tumor association of the source genes. Moreover, the peptides themselves are strongly over-presented on tumor tissue—"tumor tissue" in relation to this invention shall mean a sample from a patient suffering from myeloma, but not on normal tissues.

HLA-bound peptides can be recognized by the immune system, specifically T lymphocytes. T cells can destroy the cells presenting the recognized HLA/peptide complex, e.g. myeloma cells presenting the derived peptides.

The peptides of the present invention have been shown to be capable of stimulating T cell responses and/or are over-presented and thus can be used for the production of antibodies and/or TCRs, such as soluble TCRs, according to the present invention. Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are HAVCR1-001 peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an HAVCR1-001 peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for an HAVCR1-001 peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a HAVCR1-001 peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to HAVCR1-001 can be enhanced by methods well known in the art.

The present description further relates to a method of identifying and isolating a TCR according to the present description, said method comprising incubating PBMCs from HLA-A*02-negative healthy donors with A2/HAVCR1-001 monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with HAVCR1-001, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus post-transcriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of overcoming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 228, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of $E. coli$ such as, for example, the $E. coli$ strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, 1030, 1031, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, Juvlmmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, betaglucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomateous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualisation of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 228 according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 228, or a variant thereof which is at least 88% homologous (preferably identical) to SEQ ID NO: 1 to SEQ ID NO: 228 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 228 or a variant thereof which is at least 88% homologous (preferably identical) to SEQ ID NO: 1 to SEQ ID NO: 228, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 228.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of myeloma.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 228 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are myeloma cells or other solid or hematological tumor cells.

The present invention further relates to particular marker proteins and biomarkers based on the peptides according to the present invention, herein called "targets" that can be used in the diagnosis and/or prognosis of myeloma. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a myeloma marker (poly)peptide, delivery of a toxin to a myeloma cell expressing a cancer marker gene at an increased level, and/or inhibiting the activity of a myeloma marker polypeptide) according to the invention.

Whenever possible, the antibodies of the invention may be purchased from commercial sources. The antibodies of the invention may also be generated using well-known methods. The skilled artisan will understand that either full length myeloma marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 228 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the myeloma marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed lung cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating myeloma, the efficacy of the therapeutic antibody can be assessed in various ways well known to the skilled practitioner. For instance, the size, number, and/or distribution of lung cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of lung cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 228, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al. (Porta et al., 1994) who describe the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 228.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from myeloma, the medicament of the invention is preferably used to treat myeloma.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in myeloma cells of patients with various HLA-A HLA-B and HLA-C alleles. It may contain MHC class I and MHC class II peptides or elongated MHC class I peptides. In addition to the tumor associated peptides collected from several myelomas, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, myeloma samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the myeloma compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from myeloma patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumine). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from myeloma cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for myeloma. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

Figure 1B:
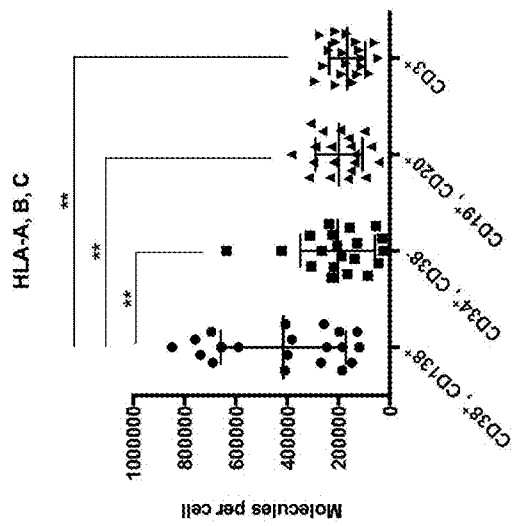
Figures 1C, 1D:
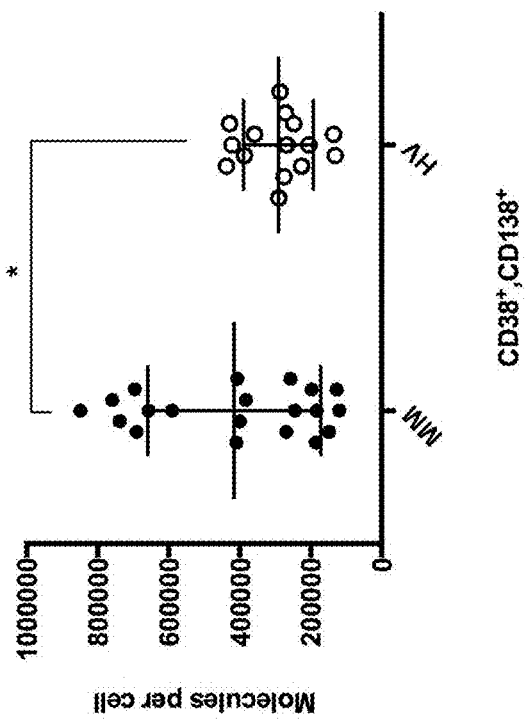

As loss or down-regulation of HLA expression on target cells might severely hamper the effectiveness of T-cell based immunotherapy, the inventors quantified HLA class I and II surface molecule counts on primary myeloma cells compared to autologous hematopoietic cells and plasma cells derived from the bone marrow of HVs. In MM patients (n=20) HLA class I expression was found to be heterogeneous with mean expression levels on CD38+CD138+myeloma cells of 416,000±54,500, which was found to be significantly higher as compared to autologous normal CD1 g+cD20+ B cells (198,5000±20,500, P=0.001), CD3+ T cells (167,500±15,500, P=0.0002) and CD34+CD38-HPCs (204,000±32,500, P=0.002, FIG. 1A). In addition, HLA class I expression on primary MM cells was also found to be significantly higher than that on CD38+CD138+ plasma cells of HVs (n=15, 291,500±25,500, P<0.05; FIG. 1 C). No significant differences in HLA class I expression were observed when comparing normal B cells, T cells and HPCs of MM patients to the corresponding cell populations of HVs. HLA-DR expression levels on myeloma cells were generally found to be much lower than HLA class I levels. Mean HLA-DR surface molecule counts on myeloma cells (27,000±7,000) showed no significant difference compared to autologous HPCs (35,000±5,000) and T cells (18,000±13,000) or plasma cells of HVs (39,500±5,000) (FIGS. 1 B and 1 D). HLA-DR expression of MM patient CD1 g+cD20+B cells (104,000±7,000) was significantly higher compared to myeloma cells (P<0.0001). No correlation of HLA surface expression on myeloma cells with patient characteristics such as sex, age, disease stage, risk classification or prior therapy was observed.

Figure 2A:
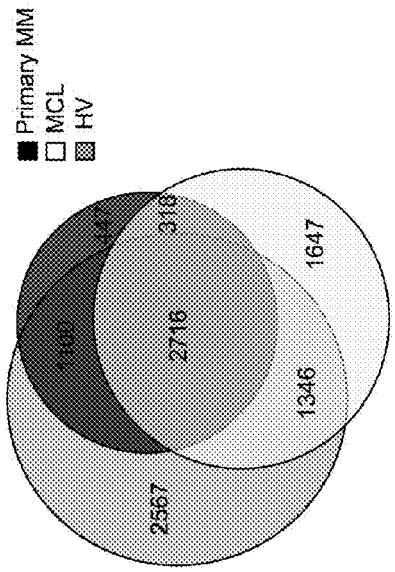

Mapping the HLA class I ligandomes of 10 myeloma patients and 5 MCLs, the inventors identified a total of 17,583 different peptides representing 7,574 source proteins, attaining >80% of the maximum attainable coverage (FIG. 2A). The mean number of unique peptide identifications was 1,059 IDs for primary myeloma samples and 2,243 IDs for MCLs. Overall, peptides restricted by 20 different HLA-A and -B allotypes were identified in this study, covering 99.3% of the Caucasian population (calculated according to [52]).

As controls, the inventors analyzed the HLA class I ligandomes of 45 HV derived samples (30 PBMC, 10 BMNC and 5 granulocyte specimens) identifying a total of 20,171 different peptides representing 7,729 source proteins. The HLA allotype distribution in the HV cohort covered >80% of HLA-A and -B alleles in the MM sample cohort [53]. Analysis of HLA class II ligandomes was performed for 7 MM patients and 5 MCLs. A total of 6,076 unique peptides representing 1,743 source proteins were identified. The HLA class II HV cohort (13 PBMC, 5 BMNC, 5 granulocyte specimens) yielded 2,899 different peptides representing 889 source proteins.

Figure 2B:
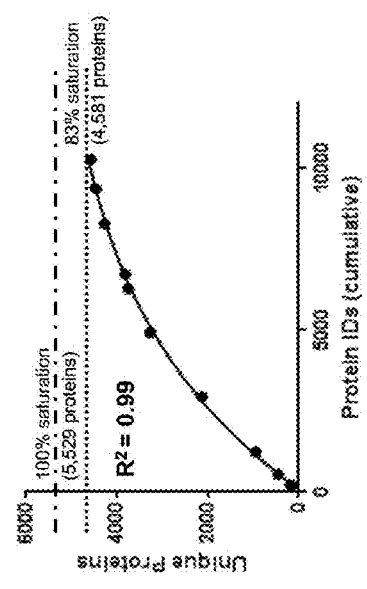
Figure 2C:
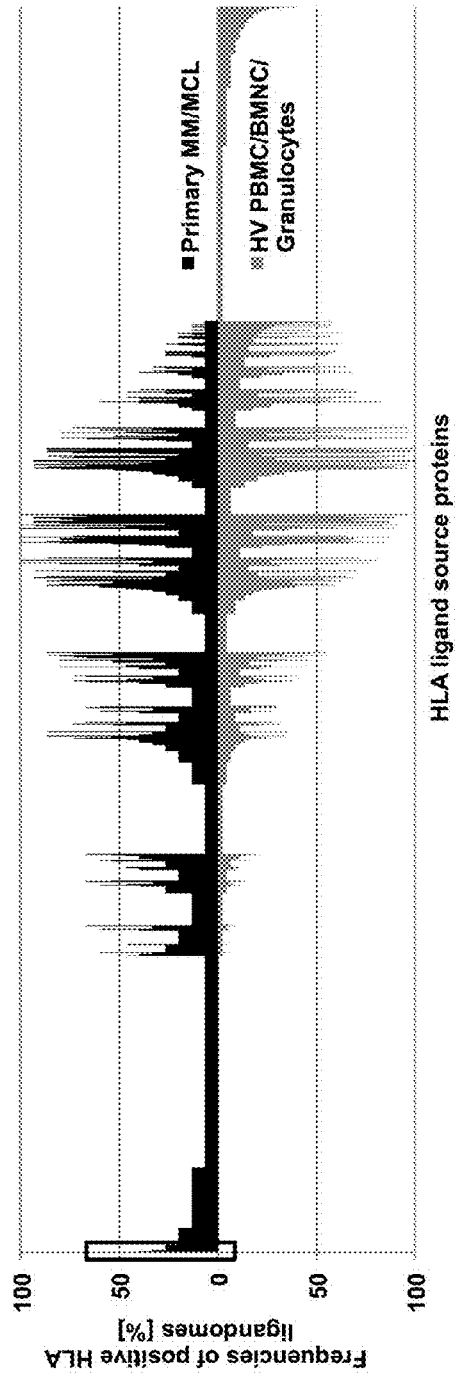
Figure 2D:
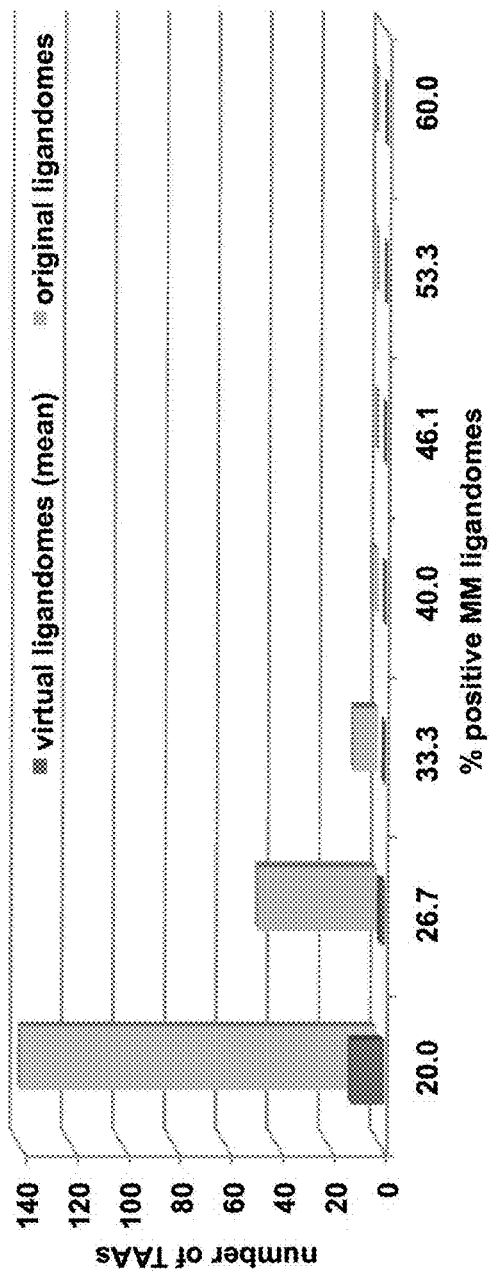

In order to identify myeloma-associated antigens the inventors comparatively analyzed the HLA ligandomes of the MM sample and HV cohorts at the source protein level. Overlap analysis of HLA ligand source proteins identified 2,412 proteins (corresponding to 31.8% of the mapped MM HLA source proteome) to be exclusively represented in the HLA ligandomes of MM samples. Of these MM-exclusive source proteins, 68.3% were solely identified on MCL samples, whereas 13.2% of proteins were found to be presented both, on MCLs and primary MM samples. A fraction of 18.5% of myeloma-exclusive source proteins was found to be restricted to primary MM samples (FIG. 2B). In order to identify broadly presented tumor-associated antigens, myeloma-exclusive source proteins were ranked according to their frequencies of representation in the MM sample cohort (FIG. 2C). To statistically assess and optimize the stringency of antigen identification, the inventors simulated randomized virtual ligandomes in silico and calculated the resultant number of false-positive TAAs at different frequencies of representation (FIG. 2D). The inventors set the frequency threshold for HLA class I tumor associated antigen ("TAA") definition to >25% of myeloma-exclusive antigen presentation, yielding 58 TAAs with an estimated false discovery rate (FDR) of 4.1%. This novel panel of frequently presented myeloma-associated antigens was represented by 197 unique HLA class I ligands and constitutes 0.8% of the mapped myeloma HLA ligand source proteome. KEGG pathway analysis [54] and functional annotation clustering of these antigens with respect to their biological function (GO Term BP FAT, [55]) did not identify any statistically significant overrepresented pathways or functional clusters. Notably, the proto-oncogene MMSET was identified as a TAA showing representation in 33% of MM patient ligandomes and was found to be represented by 3 different HLA ligands (ASNPSNPRPSK (HLA-A*30:01) (SEQ ID NO. 17), KAMEAASSL (A*02:01) (SEQ ID NO. 82), SLLEQGLVEA (A*02:01) (SEQ ID NO. 177)). Moreover, MMSET was detected on both of the two MM patients with the oncogenic translocation t(4;14), but only on 1/6 (17%) patients without this aberration.

Figure 3A:
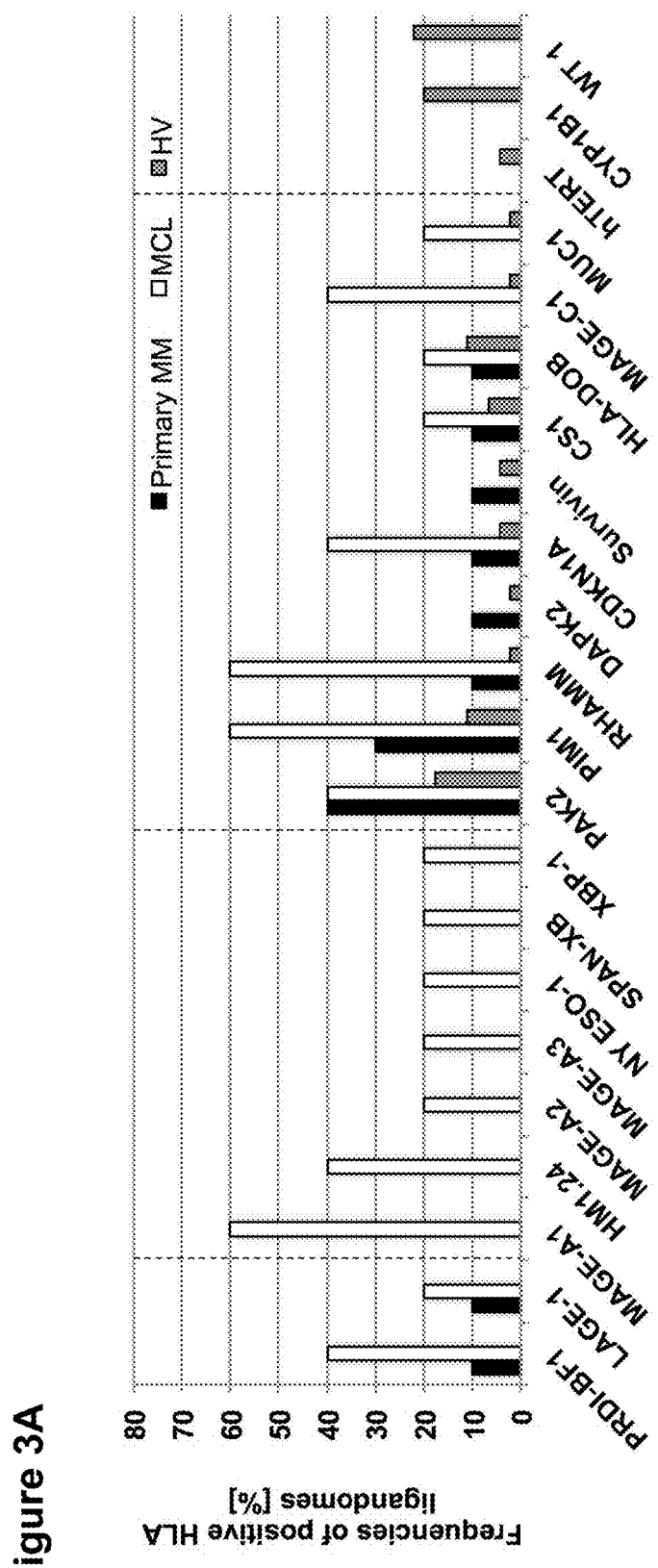
Figure 3C:
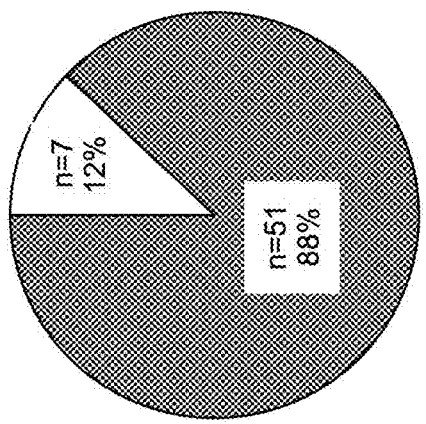
Figure 3B:
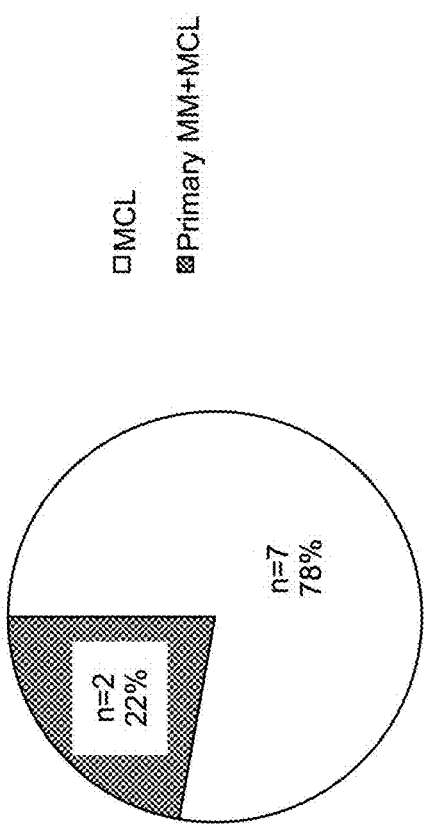

Representation of Established Myeloma-Associated Antigens in the HLA Class I Ligandome Based on the inventors' extensive HLA ligandome dataset, the inventors investigated the presentation of established myeloma-associated antigens within the different sample cohorts. The inventors identified 73 different HLA ligands representing 22/25 (88%) of previously described myeloma antigens [42]. The inventors found 9 of the 22 detectable antigens (41%) to be exclusively presented on MM samples, 10/22 (45.5%) antigens to be represented both on MM and HV samples, and 3/22 (13.6%) exclusively presented on HV derived samples (FIG. 3A). Of note, 7/9 (77.8%) MM-exclusive antigens were only detectable on MCLs. Only for 2/9 (22.2%) of these MM-exclusive antigens HLA ligands were detected on primary MM patient samples (FIG. 3B). For reference, only 7/58 (12.1%) of the newly defined myeloma antigens showed presentation exclusively on MCLs, whereas the majority of 51/58 (87.9%) of antigens was also presented on primary MM patient samples as well, which underlines their potential as clinical target antigens (FIG. 3C).

Moreover, unsupervised clustering of source protein presentation in the HLA ligandomes revealed the cluster of MCLs to be highly distinct from primary MM samples.

Analysis of HLA Class II Ligandomes Identifies Potentially Synergistic Vaccine Candidates As the direct involvement of CD4$^+$ T cells in tumor control is established [56], the inventors further aimed to identify HLA class II antigens. Overlap analysis of HLA class II ligand source proteins identified 1,135 myeloma exclusive antigens (FIG. 4A). Comparative profiling of HLA class II ligandomes identified a single antigen (TFRC) represented by 67 HLA class II ligands showing MM-exclusive presentation at FDR <5% (FIGS. 4B, 4C). Functional characterization of the most abundant TFRC peptide (NSVIIVDKNGRLV) (SEQ ID NO. 237). by IFNγ ELISPOT revealed memory T-cell responses in 2/5 MM patients.

As co4+ T cells play pivotal roles in the induction and maintenance of antigen-specific cos+ T-cell responses [57-59], the inventors implemented a second approach to identify potentially synergistic HLA class II restricted peptides derived from HLA class I TAAs. Overlap analysis of the 58 HLA class I antigens with the 1,135 H LA class II presented MM exclusive proteins identified a panel of 6 class-spanning antigens, including APVGIMFLVAGKIVE (SEQ ID NO: 16), MPDDSYMVDYFKSISQ (SEQ ID NO: 123), GYPTIKILKKGQAVDYEG (SEQ ID NO: 64), VPVGGLSFLVNHDFSPL (SEQ ID NO: 215), and IVDRTTTVVNVEG (SEQ ID NO: 80), represented by 31 peptides (FIGS. 4D, 4E; Table 5A). Functional characterization of synergistic HLA class II ligands revealed peptide-specific T-cell responses in myeloma patients for 3/5 tested peptides (FIG. 4E).

The overall comparison of the HLA class I and II ligandomes of MM samples revealed 80% (1,622) of HLA class II presented proteins to be also presented on HLA class I (FIG. 4F). Functional annotation clustering (GO Term CC clustering using DAVID [55]) was performed on the top 500 most frequently presented proteins in each HLA class to identify the cellular compartments from which these proteins derive. Antigens presented on class I displayed highly enriched clusters for nuclear proteins as well as for ribosomal, cytoskeletal and vesicle-derived proteins. Notably, this pattern was recapitulated in the clustering of proteins presented on both HLA classes, albeit with a higher ranking and an almost 3-fold higher enrichment for vesicle-derived proteins. HLA class II presented antigens showed intermediate enrichment for plasma membrane, vesicle-derived and lysosomal proteins.

HLA class I TAAs are targeted by spontaneous T-cell responses in myeloma patients Functional characterization of the novel myeloma antigens was performed in panels of 11 HLA-A*02 and 2 HLA-B*07 restricted peptides, including 2 HLA-A*02 ligands derived from MMSET, e.g., KAMEAASSL (SEQ ID NO: 82) and SLLEOGLVEA (SEQ ID NO: 177), one HLA-A*02 ligand derived from SLC 1A5, e.g., FVFPGELLL (SEQ ID NO: 51), one HLA-A*02, ligand derived from SEMA4A, e.g., FLFQLLQLL (SEQ ID NO: 48), one HLA-B*07 ligand derived from SLXIA, e.g., LPPPPHVPL (SEQ ID NO: 115), and one HLA-A*02 ligand derived from SLXIA, e.g., LAHVGPRL (SEQ ID NO: 108) (FIG. 5A). Myeloma-associated peptides were evaluated in 12-day recall IFNγ ELISPOT assays using PBMC obtained from MM patients and HVs. The inventors observed IFNγ secretion for 5/11 A*02 ligands and 1/2 B*07 ligands in myeloma patients, as shown exemplarily in FIG. 5C. Both peptides ($P_1$ and $F_2$) derived from MMSET showed specific T-cell recognition in 2/16 (13%) and 1/8 (13%) of MM patients, respectively. Importantly, no myeloma peptide-specific IFNγ secretion was observed in 10 HLA-matched healthy controls (FIG. 5B). Notably, T-cell responses were only observed for myeloma-associated peptides identified on primary myeloma samples (10/13), and never for the 3/13 peptides identified on MCLs only. The frequencies of peptide-specific T-cell responses detected in MM patients by ELISPOT were generally in the same range as the frequencies of presentation of the respective peptide in allotype-matched ligandomes of MM patients (FIG. 5A). Due to limitations in the numbers of cells available for analysis, further controls with target cells expressing the corresponding antigens could not be performed. The inventors therefore cannot exclude that T-cell reactivity is directed against impurities contained in the synthetic peptide batch. Indeed, it is well known that synthetic peptides contain impurities, e.g. peptides modified with a protecting group, and that these impurities are immunogenic. However, HLA-A*02 and -B*07 restricted control peptides derived from benign tissues (HV exclusive HLA ligands) used in all ELISPOTs in the study at hand did never result in significant IFNγ release (FIG. 5C).

Figures 5D, 5E:
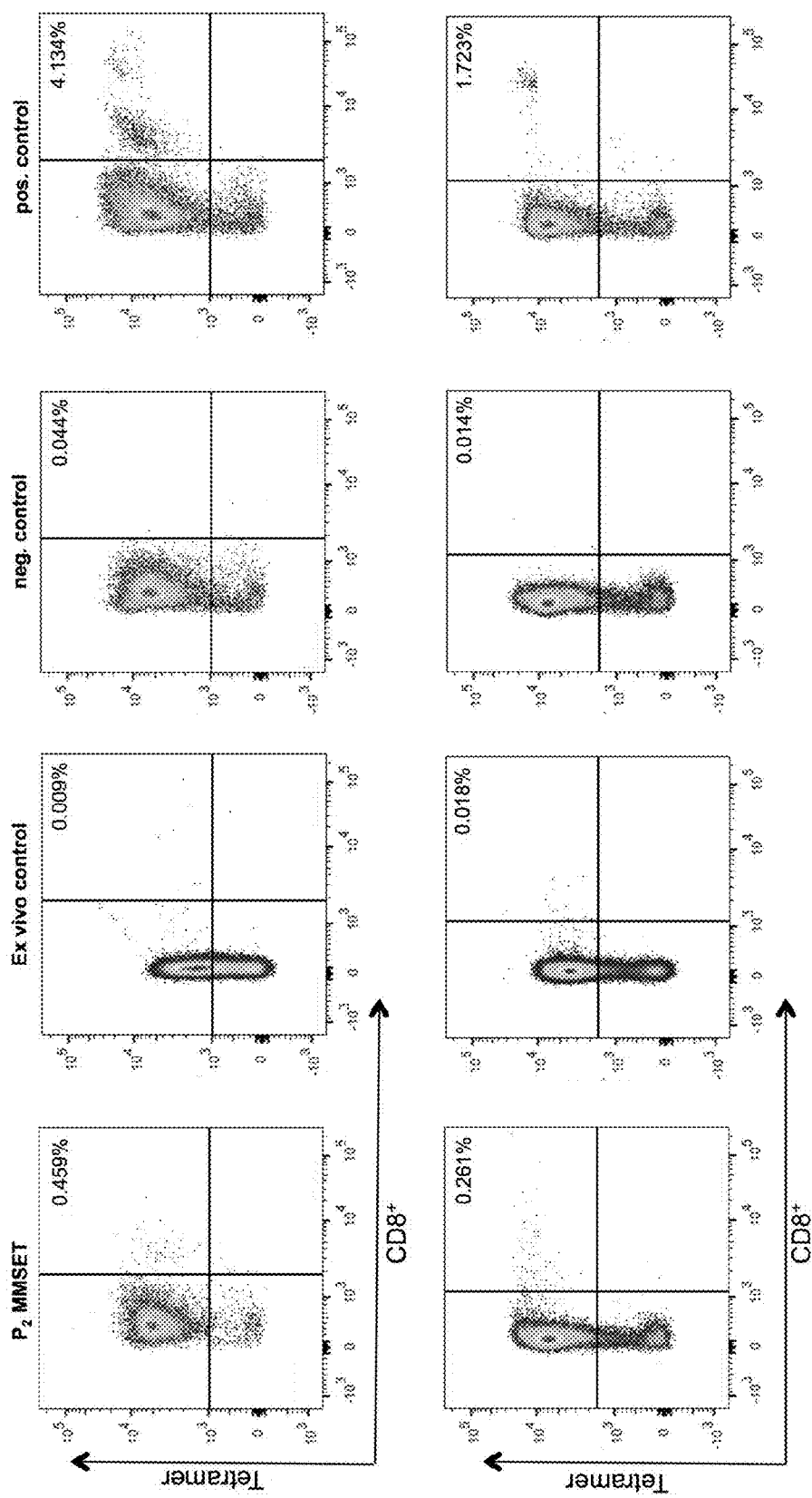

Antigen-Specific T Cells can be Induced In Vitro from Naïve T Cells of MM Patients or HVs To assess whether myeloma antigen-specific T-cell responses can be induced from naïve T cells in vitro the inventors isolated CD8+ T cells from one healthy individual and one MM patient. The inventors performed aAPC-primings using the MMSET-derived peptide SLLEQGLVEA (SEQ ID NO. 177) ($P_2$). Using HV-derived CD8+ T cells, a population of 0.403% $P_2$-tetramer positive CD8+ T cells was detected after in vitro priming. No tetramer-positive T-cell populations >0.1% were detectable ex vivo. After priming of T cells from an MM patient without previous T-cell reactivity for P2 (as detected by 12d-recall IFNγ-ELISPOT and ex vivo tetramer staining), the inventors detected the induction of a small population of 0.236% $P_2$-tetramer positive CD8+ T cells (FIG. 5E). Importantly, control stainings performed with an A*02-tetramer containing a non-relevant A*02 control peptide were performed in parallel on cells derived from the same wells as used for the relevant staining and did not yield any specific tetramer-positive T-cell populations (FIG. 5D).

Quantification of HLA surface expression on different cell populations in the bone marrow of myeloma patients and healthy volunteers demonstrated that HLA-loss or down-regulation on malignant plasma cells is of no concern, even in patients who received prior therapy. Comparative analysis of the HLA ligandomes of these cell populations revealed distinct antigenic signatures and identified a panel of myeloma-associated antigens.

Importantly, a substantial proportion of established myeloma-antigens were found to be only infrequently presented on primary myelomas or to show suboptimal degrees of myeloma-specificity. Of note, the majority of these antigens were selectively detected on myeloma cell lines but not in primary samples, indicating that selection of pathophysiologically relevant antigens should be based on analysis of primary tumor samples.

A notable exception was the established myeloma-associated protein MMSET, which is currently being investigated as a target for the therapy of poor-prognosis t(4;14) myeloma patients [73-76]. Although MMSET-derived peptides were frequently identified on t(4;14) myeloma samples, the inventors also detected MMSET peptides in the HLA ligandomes of a t(4;14)-negative patient and one t(4;14)-negative MCL (U266). Strikingly, functional characterization by ELISPOT revealed memory T-cell responses targeting these MMSET-derived epitopes exclusively in myeloma patients and not in HV. This suggests myeloma-dependent priming of anti-MMSET T-cell responses in vivo in MM patients, which underscores the pathophysiological relevance of this antigen. In concordance with the HLA ligandomics data, the inventors found these T-cell responses not to be restricted to t(4;14) myeloma patients. Results of in vitro primings suggest that MMSET-specific CD8+ T-cell responses can be induced from naïve T cells, both in healthy individuals and, importantly, also in myeloma patients, albeit with limited magnitudes. With the current strategies focusing on inhibition of MMSET by small molecules or siRNAs [77, 78], the inventors' identification of myeloma-exclusive MMSET-derived T-cell epitopes provides new options for targeting MMSET by T-cell based immunotherapy. Notably, this therapeutic strategy may not necessarily have to be restricted to t(4;14) myelomas, as the inventors observed MMSET-presentation and immune recognition irrespective of the mutational status. This might be explained by the distorted correlation of gene expression and HLA restricted antigen presentation as well as by the subclonal distribution of t(4;14) in myeloma cells and genomic plasticity occurring over the course of disease [72, 79].

Together, the inventors' findings illustrate how antigen identification guided by HLA ligandomics can pinpoint novel MM-associated T-cell epitopes and allows to directly assessing antigen distribution patterns in patient cohorts. In parallel to the inventors' findings with MMSET, the inventors' study features an extensive panel of novel antigens previously not associated with myeloma or cancer in general. Analogously to MMSET, the inventors detected pre-existing T cell responses against a substantial proportion of these targets in myeloma patients, indicating a high enrichment for relevant MM-associated antigens. In conclusion, the inventors' ligandome-centric study may guide the design of future antigen-specific T-cell immunotherapy in multiple myeloma.

The present invention will now be described in the following examples which describe preferred embodiments thereof, and with reference to the accompanying figures, nevertheless, without being limited thereto. For the purposes of the present invention, all references as cited herein are incorporated by reference in their entireties.

FIGURES

FIGS. 1A to 1D show the HLA class I & II surface expression on myeloma patient and HV bone marrow cells. Quantification of HLA surface expression was performed using a bead-based flow cytometric assay. (FIG. 1A) HLA class I and (FIG. 1B) HLA-DR expression on CD38+ CD138+ primary myeloma cells compared to autologous CD34+CD38− hematopoietic progenitor cells, CD19+CD20+ B cell and CD3+ T cells. (FIG. 1C) HLA class I and (FIG. 1D) HLA-DR expression on primary MM cells compared to bone marrow-derived plasma cells of HVs. Abbreviations: MM, multiple myeloma; HV, healthy volunteers; n.s., not significant; *P<0.05, P<0.01, *P<0.001

FIGS. 2A to 2D show the comparative HLA ligandome profiling and identification of myeloma associated antigens. (FIG. 2A) Saturation analysis of HLA class I ligand source protein identifications in MM patients. Number of unique HLA ligand source protein identifications as a function of cumulative HLA ligand source protein identifications in 10 MM patients. Exponential regression allowed for the robust calculation ($R^2$=0,99) of the maximum attainable number of different source protein identifications (dashed line). The dotted line depicts the source proteome coverage achieved in the inventors' MM patient cohort. (FIG. 2B) Overlap analysis of HLA class I ligand source proteins of primary MM samples (n=10), MCLs (n=5) and HV samples (total n=45: PBMC (n=30), BMNC (n=10), granulocytes (n=5)). (FIG. 2C) Comparative profiling of HLA ligand source proteins based on the frequency of HLA restricted presentation in MM and HV ligandomes. Frequencies of MMs/HVs positive for HLA restricted presentation of the respective source protein (x-axis) are indicated on the y-axis. The box on the left highlights the subset of myeloma-associated antigens showing MM-exclusive presentation in >25% of myeloma samples. (FIG. 2D) Statistical assessment of false-positive myeloma-antigen identifications at different threshold values. The numbers of original TAAs identified based on the analysis of the MM and HV cohorts were compared with random virtual TAAs. Virtual MM and HV samples were generated in silico based on random weighted sampling from the entirety of protein identifications in both original cohorts. These randomized virtual ligandomes of defined size (n=957 proteins, which is the mean number of protein identifications in all analyzed samples) were used to define TAAs based on simulated cohorts of 15 MM versus 45 HV samples. The process of protein randomization, cohort assembly and TAA identification was repeated 1,000 times and the mean value of resultant virtual TAAs was calculated and plotted for the different threshold values. The corresponding false discovery rates for any chosen TAA threshold are listed below the x axis. Abbreviations: ID, identifications; MM, multiple myeloma; MCL, myeloma cell line; HV, healthy volunteer; PBMC, peripheral mononuclear blood cell; BMNC, bone marrow mononuclear cell; TAA, tumor-associated antigen; sum, summary; FDR, false discovery rate.

FIGS. 3A to 3C show the representation of established myeloma-associated antigens in the HLA ligandomes of MM and HV. (FIG. 3A) Representation of previously described MM-associated antigens in HLA class I ligandomes. Bars indicate relative representation [%] of respective antigens by HLA class I ligands on primary MM samples, MCLs and HV samples. Dashed lines divide the antigens into 4 groups according to their degree of MM-association (MM & MCL-exclusive, MCL-exclusive, mixed presentation, HV-exclusive). (FIGS. 3B, 3C) Distribution of myeloma-exclusive antigen presentation for (FIG. 3B) previously described antigens and (FIG. 3C) ligandome-defined tumor-associated antigens on MCLs (white) and MM+MCLs (shaded). Abbreviations: MM, multiple myeloma; MCL, myeloma cell line; HV, healthy volunteer.

FIGS. 4A to 4F shows the identification of synergistic HLA class II restricted myeloma-associated antigens. (FIG. 4A) Overlap analysis of HLA class II ligand source proteins of primary MM samples (n=7), MCLs (n=5) and HV samples (total n=23: PBMC (n=13), BMNC (n=5), granulocytes (n=5)). (FIG. 4B) Statistical analysis of false-positive myeloma-antigen identifications at different threshold values, as described in FIG. 2. Randomized virtual ligandome sizes were set to 226 proteins and TAAs were defined based on simulated cohorts of 12 MM versus 23 HV samples. (FIG. 4C) Comparative profiling of HLA class II ligand source proteins based on the frequency of HLA restricted presentation in MM and HV ligandomes. Frequencies of MMs/HVs positive for HLA restricted presentation of the respective source protein (x-axis) are indicated on the y-axis. (FIG. 4D) Overlap analysis of HLA class I TAAs (n=58) and HLA class II MM-exclusive antigens (n=1135). (FIG. 4E) HLA class I TAAs, which also yield potentially synergistic HLA class II ligands. (FIG. 4F) Overlap analysis comprising the entire HLA class I and II ligand source proteomes of MM samples. Abbreviations: MM, multiple myeloma; MCL, myeloma cell line; HV, healthy volunteer; PBMC, peripheral mononuclear blood cell; BMNC, bone marrow mononuclear cell; TAA, tumor-associated antigen; sum, summary; FDR, false discovery rate; rep., representation.

FIGS. 5A to 5E show the functional characterization of myeloma-associated antigens. (FIG. 5A) Myeloma-associated T cell epitopes with their corresponding HLA restrictions and frequencies of immune recognition by myeloma patient derived T cells in IFNγ-ELISPOT assays. (FIG. 5B) Example of myeloma-associated T cell epitopes evaluated in an IFNγ-ELISPOT using HV PBMC. An EBV epitope mix containing the frequently recognized peptides BRLF109-117 YVLDHLIW (A*02) (SEQ ID NO. 229) and EBNA3247-255 RPPIFIRRL (SEQ ID NO. 230) (B*07 served as positive control. Benign-tissue derived peptides KLFEKVKEV (SEQ ID NO. 231) (HLA-A*02) and KPSEKIQVL (B*07) (SEQ ID NO. 232) served as negative control. (FIG. 5C) Examples of myeloma-associated T cell epitopes evaluated in IFNγ-ELISPOTs using MM patient PBMC (n=3). Results are shown only for immunoreactive peptides. An EBV epitope mix containing five frequently recognized peptides [BRLF109-117 YVLDHLIW (A*02) (SEQ ID NO. 229), EBNA3471-479 RLRAEAQVK (A*03) (SEQ ID NO. 233), EBNA3247-255 RPPIFIRRL (B*07) (SEQ ID NO. 230), BZLF1190-197 RAKFKQLL (B*08) (SEQ ID NO. 234), EBNA6162-171 AEGGVGWRHW (B*44) (SEQ ID NO. 235)] was used as positive control. Benign-tissue derived peptides KLFEKVKEV (SEQ ID NO. 231) (HLA-A*02) and KPSEKIQVL (B*07) (SEQ ID NO. 232) served as negative control. (FIGS. 5D, 5E) Tetramer staining of CD8$^+$ T cells after 3 cycles of aAPC-based in vitro primings using T cells derived from (FIG. 5D) a healthy individual and (FIG. 5E) a myeloma patient: $1^{st}$ column: $P_2$-tetramer staining of CD8$^+$ T cells primed with $P_2$-aAPCs (SLLEQGLVEA, A*02 (SEQ ID NO. 177)); $2^{nd}$ column: ex vivo $P_2$-tetramer staining of CD8$^+$ T cells; $3^{rd}$ column: control staining with A*02-tetramer containing a non-relevant A*02 restricted control peptide (KAMEAASSL, A*02 (SEQ ID NO. 82)) on CD8$^+$ T cells derived from the same population as T cells depicted in the $1^{st}$ column. $4^{th}$ column: positive control: tetramer staining of CD8$^+$ T cells primed with CMV-aAPCs (NLVPMVATV, A*02 (SEQ ID NO. 236)). Abbreviations: MM, multiple myeloma; UPN, uniform patient number; neg., negative; pos., positive.

Figure 6A:
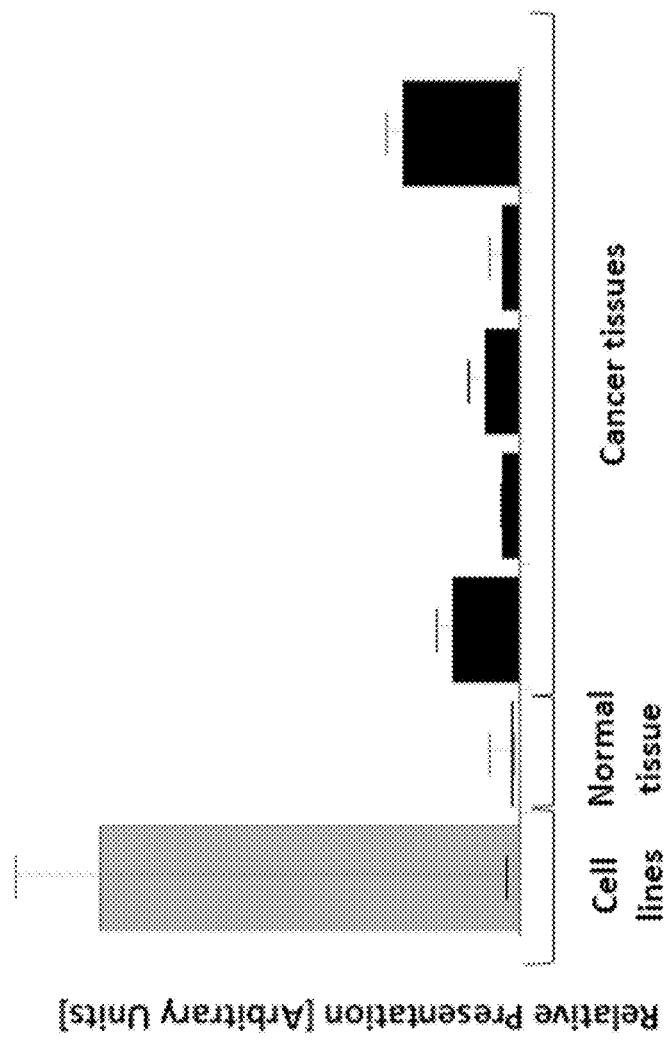
Figure 6B:
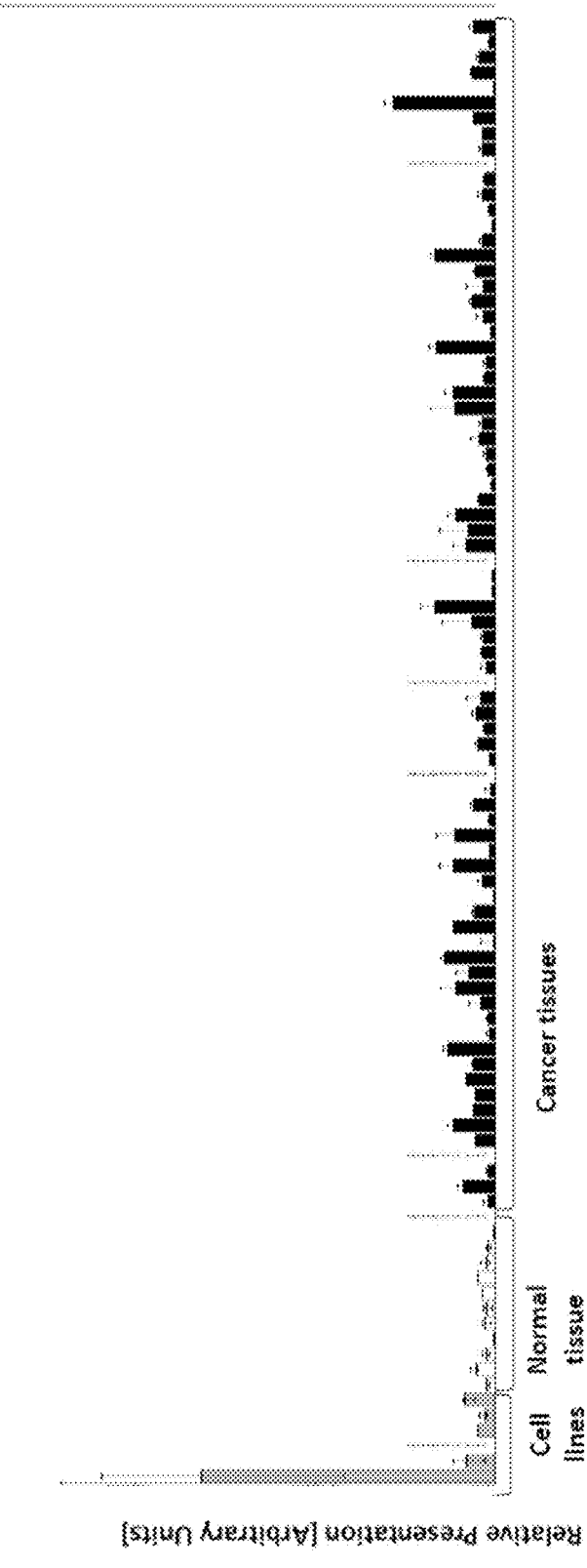

FIGS. 6A and 6B show presentation of peptides SEQ ID NO: 107 and 177 on tissues other than myeloma. FIG. 6A) Normal tissues tested negative for the peptide were: 6 adipose tissues, 8 adrenal glands, 24 blood cell samples, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 11 spleens, 8 stomachs, 5 testes, 3 thymi, 5 thyroid glands, 16 tracheas, 7 ureters, 8 urinary bladders, 6 uteri. In addition to MM, the peptide was found presented on: 1 cell line (melanoma), 1 normal tissue (spleen), 5 cancer samples (AML, 2 gallbladder cancers, 1 hepatocellular carcinoma, 1 melanoma). FIG. 6B) Normal tissues tested negative for the peptide were: 6 adipose tissues, 8 adrenal glands, 24 blood cell samples, 15 blood vessels, 10 bone marrows, 9 brains, 7 breasts, 9 esophagi, 2 eyes, 3 gallbladders, 16 hearts, 17 kidneys, 23 large intestines, 24 livers, 49 lungs, 7 lymph nodes, 10 nerves, 3 ovaries, 13 pancreases, 6 parathyroid glands, 1 peritoneum, 6 pituitary glands, 7 placentas, 1 pleura, 3 prostates, 7 salivary glands, 9 skeletal muscles, 11 skins, 8 small intestines, 11 spleens, 8 stomachs, 5 testes, 3 thymi, 5 thyroid glands, 15 tracheas, 7 ureters, 8 urinary bladders, 6 uteri. In addition to MM, the peptide was found presented on: 6 cell-lines (5 leukemias, 1 kidney cancer), 4 brains, 1 central nerve, 2 colons, 1 peripheral nerve, 1 prostate, 1 small intestine, 1 spleen, 1 trachea, 1 bile duct cancer, 12 brain cancers, 2 breast cancers, 3 colon cancers, 4 esophageal cancers, 3 gallbladder cancers, 4 head-and-neck cancers, 2 kidney cancers, 2 liver cancers, 19 lung cancers, 2 NHL, 1 AML, 8 ovarian cancers, 2 prostate cancers, 1 rectum cancer, 4 skin cancers, 2 urinary bladder cancers, 6 uterus cancers.

EXAMPLES

Materials and Methods

Patients, Blood and Bone Marrow Samples

Bone marrow mononuclear cells (BMNC) and peripheral blood mononuclear cells (PBMC) from MM patients at the time of diagnosis or at relapse before therapy, as well as PBMCs, BMNCs and granulocytes of healthy volunteers (HV), were isolated by density gradient centrifugation (Biocoll, Biochrom GmbH) and erythrocyte lysis (EL buffer, Qiagen). Informed consent was obtained in accordance with the Declaration of Helsinki protocol. The study was performed according to the guidelines of the local ethics committee (142/2013602). Patient characteristics are provided in table 1. HLA typing was carried out by the Department of Hematology and Oncology, Tubingen, Germany.

Myeloma Cell Lines (MCL)

For HLA ligandome analysis myeloma cell lines (MCLs: U266, RPM18226, JJN3, LP1, MM.1S) were cultured in the recommended cell media (RPM11640, Gibco/IMDM, Lonza) supplemented with 10%/20% fetal calf serum, 100 IU/L penicillin, 100 mg/L streptomycin, and 2 mmol/L glutamine at 37° C. and 5% $CO_2$. The MCLs RPM18226, JJN3, MM.1S and LP-1 were obtained from the Department of Hematology and Oncology, Tubingen.

Quantification of HLA Surface Expression

HLA surface expression on MM patient and HV bone marrow cells including $CD38^+CD138^+$ myeloma cells/plasma cells, $CD19^+CD20^+$ B cells, $CD3^+$ T cells and $CD34^+CD38^-$ hematopoietic progenitor cells (HPC) were analyzed using the QIFIKIT bead based quantitative flow cytometric assay (Dako) according to manufacturer's instructions as described before [12]. In brief, sample were stained with the pan-HLA class I specific monoclonal antibody (mAb) W6/32, HLA-DR specific mAb L243 (produced in house) or IgG isotype control (BioLegend), respectively. Surface marker staining was carried out with directly labeled CD138, anti-K, anti-A, CD19, CD20 (BioLegend) and CD38, CD3 and CD34 (BD) antibodies. 7-AAD (BioLegend) was added as viability marker immediately before flow cytometric analysis on a LSR Fortessa (BD).

Isolation of HLA Ligands from Primary Samples and MCLs

HLA class I and II molecules were isolated using standard immunoaffinity purification as described [44] using the pan-HLA class I specific mAb W6/32, the pan-HLA class II specific mAb Tü39 and the HLA-DR specific mAB L243 (produced in house).

Analysis of HLA Ligands by LC-MS/MS

HLA ligand extracts were analyzed in 5 technical replicates as described previously [13]. In brief, peptide samples were separated by nanoflow HPLC (RSLCnano, ThermoFisher) using a 50 μm×25 cm PepMap RSLC column (Thermo Fisher) and a gradient ranging from 2.4 to 32.0% acetonitrile over the course of 90 min. Eluting peptides were analyzed in an online coupled LTQ Orbitrap XL mass spectrometer (Thermo Fisher) using a top 5 CID (collision induced dissociation) fragmentation method.

Database Search and Spectral Annotation

Data processing was performed as described previously [13]. In brief, the Mascot search engine (Mascot 2.2.04; Matrix Science, London, UK) was implemented to search the human proteome as comprised in the Swiss-Prot database (20,279 reviewed protein sequences, September 2013) without enzymatic restriction. Potential mutated HLA ligands were searched implementing a database containing the human proteome concatenated with proteins containing single amino acid variants (SAVs) listed in the COSMIC database (http://cancer.sanger.ac.uk/cosmic/). Only recurrent SAVs described in 2 or more samples of hematological origin were included. Oxidized methionine was allowed as a dynamic modification. The false discovery rate was estimated using the Percolator algorithm [45] and set to 5%. Peptide lengths were limited to 8-12 amino acids for HLA class I and 12-25 amino acids for HLA class II. Protein inference was disabled, allowing for multiple protein annotations of peptides. HLA annotation was performed using SYFPEITHI [46] or an extended in-house database. Experimental validation of peptide identifications and HLA annotations was performed by mass spectrometric and functional characterization of synthetic peptides for a subset of peptides.

Peptide and HLA Peptide Monomer Synthesis

The automated peptide synthesizer EPS221 (Abimed) was used to synthesize peptides using the 9-fluorenylmethyl-oxycarbonyl/tert-butyl (Fmoc/tBu) strategy [47]. Synthetic peptides were used for validation of LC-MS/MS identifications as well as for functional experiments. Biotinylated recombinant HLA molecules and fluorescent MHC-peptide-tetramers were produced as described previously [48].

Amplification of Peptide-Specific T Cells

PBMC from MM patients and HVs were cultured as described previously [12, 13]. In brief, for $CD8^+$ T-cell stimulation, PBMC were pulsed with 1 μg/ml per peptide and cultured for 12 days adding IL-4 and IL-7 on day 0 and 1 as well as IL-2 on day 3, 5, 7 and 9. HLA-A*02 (KLFEKVKEV) (SEQ ID NO. 231) and B*07 (KPSEKIQVL) (SEQ ID NO. 232) restricted control peptides derived from benign tissues (HV-exclusive HLA ligands) served as negative control. Peptide-stimulated PBMC were analyzed by ELISPOT assays on day 12. For $CD4^+$ T-cell stimulation, culture was performed as described for $CD8^+$ T cells except for 2 modifications: pulsing was carried out with 10 μg/ml of HLA class II peptide and no IL-4 or IL-7 was added.

IFNγ ELISPOT Assay

IFNγ ELISPOT assays were carried out as described previously [49]. In brief, 96-well nitrocellulose plates (Millipore) were coated with 1 mg/ml IFNγ mAb (Mabtech) and incubated over night at 4° C. Plates were blocked with 10% human serum for 2 h at 37° C. $2.5 \times 10^5$ cells/well of pre-stimulated PBMC were pulsed with 1 μg/ml (HLA class I) or 2.5 μg/ml (HLA class II) peptide and incubated for 24-26 h. Readout was performed according to manufacturer's instructions. PHA was used as positive control. HLA-A*02 (KLFEKVKEV) (SEQ ID NO. 231) and B*07 (KPSEKIQVL) (SEQ ID NO. 232) restricted control peptides derived from benign tissues (HV-exclusive HLA ligands) served as negative control. Spots were counted using an ImmunoSpot S5 analyzer (CTL). T cell responses were considered to be positive when >10 spots/well were counted and the mean spot count per well was at least 3-fold higher than the mean number of spots in the negative control wells (according to the cancer immunoguiding program (CIP) guidelines [50]).

aAPC Priming of Peptide-Specific T Cells

For the generation of artificial antigen presenting cells (aAPC), $4 \times 10^6$ streptavidin-coated polystyrene particles (Bangs Laboratories) per ml were resuspended in PBE (PBS/BSA/ETDA, Gibco/Sigma Aldrich/Lonza) containing 200 μM biotinylated MHC-peptide monomer and 20 nM anti-human biotinylated CD28 antibody and incubated at room temperature for 30 min. After washing, the aAPCs were stored at 4° C. prior to use [51]. $CD8^+$ T cells from MM patients and HV were enriched by positive selection using magnetic cell sorting (Miltenyi Biotec). Stimulations were initiated in 96-well plates with 1×10⁶ T cells plus 2×10⁵ aAPCs in 200 μl T-cell medium complemented with 5 ng/ml human IL-12 (PromoKine). 65 U/μl IL-2 (R&D Systems) were added on day 5. aAPC stimulation was repeated on day 10, for a total of 3 cycles.

Tetramer Staining

The frequency of peptide-specific CD8⁺ T cells was determined on a FACS Canto II cytometer (BD Bioscience) by staining with anti-CD8 (Biolegend) and HLA:peptide-tetramer-PE as described previously [51]. Staining with tetramers containing the CMV pp65 A*02 peptide NLVP-MVATV (SEQ ID No. 236) served as positive control, tetramers containing irrelevant, non-primed A*02 restricted control peptides as negative controls. Successful priming was considered if frequency of peptide-specific CD8⁺ T cells was >0.1% of viable cells and at least 3-fold higher than the frequency of peptide-specific CD8⁺ T cells in the negative control.

Software and Statistical Analysis

Flow cytometric data analysis was performed using FlowJo 7.2 (Treestar). In-house R and Python scripts were used for the generation of virtual ligandomes and definition of virtual TAAs (tumor-associated antigens) in the analysis of TAA false discovery rates and for the TAA-plateau regression analysis. The standard R heatmap.2 script was used for the unsupervised cluster analysis of HLA ligand source proteins. Graph Pad Prism 6.0 (Graph Pad Software) was used for statistical analysis. Statistical analysis of HLA surface expression was based on unpaired t-tests.

HLA Class I Ligand Presentation During Proteasome Inhibitor Therapy.

The inventors quantitatively assessed HLA class I ligand presentation during proteasome inhibitor therapy. Observed was a considerable plasticity of the HLA class I ligandome after treatment with carfilzomib with 17.9±1.1% of MM.1S ligands and 11.2±0.7% of U266 ligands (mean of three biological replicates±s.d.) showing significant modulation (fold-change ≥4, P<0.01 after Benjamini-Hochberg correction) at t24 h compared with mock-treated controls. Briefly, Cultured MCLs (MM.1S and U266) and primary myeloma samples were incubated with carfilzomib (100 nM, Kyprolis®, available, e.g., from Onyx Pharmaceuticals, Inc.) as an example for a proteasome inhibitor for a 1-h period, followed by three washes in PBS (Gibco) and recultured for additional 24 or 48 h. Controls were incubated with vehicle control (glucose 5%) for 1 h, followed by identical washing and incubation for 24 or 48 h. Experiments were conducted in three biological replicates where indicated. The results are shown in the following tables.

TABLE 5A

Myeloma-associated peptides as detected on MM.1S cells and their modulation upon carfilzomib-treatment

| Myeloma LiTAP | HLA | SEQ ID NO | 24#1 | 24#2 | 24#3 | 48#1 | 48#2 | 48#3 |
|---|---|---|---|---|---|---|---|---|
| RYLDLFTSF | A*24:02 | 161 | -1 | -1 | -1 | 0 | -1 | -1 |
| AFIQAGIFQEF | A*23:01 | 4 | -1 | 0 | -1 | 0 | 0 | -1 |
| SEFDFFERL | C*12:03 | 165 | 0 | 0 | 0 | 0 | 0 | -1 |
| YVFPGVTRL | C*12:03 | 227 | 0 | 0 | 0 | -1 | 0 | 0 |
| TFLPFIHTI | A*23:01 | 196 | 0 | 0 | 0 | 0 | 0 | 0 |
| RYFKGPELL | A*24:02 | 160 | 0 | 0 | 0 | 0 | 0 | 0 |
| RYSPVLSRF | A*24:02 | 163 | 0 | 0 | 0 | 0 | 0 | 0 |
| RYSTQIHSF | A*24:02 | 164 | 0 | 0 | 0 | 0 | 0 | 0 |
| SYLNSVQRL | A*24:02 | 192 | 0 | 0 | 0 | 0 | 0 | 0 |
| YYLNEIQSF | A*24:02 | 228 | 0 | 0 | 0 | 0 | 0 | 0 |
| NEFPVFDEF | B*18:01 | 128 | 0 | 0 | 0 | 0 | 0 | 0 |
| IPAKPPVSF | B*42:01 | 76 | 0 | 0 | 0 | 0 | 0 | 0 |
| RPHGGKSL | B*42:01 | 149 | 0 | 0 | 0 | 0 | 0 | 0 |
| RPQLKGVVL | B*42:01 | 151 | 0 | 0 | 0 | 0 | 0 | 0 |
| SPALPGLKL | B*42:01 | 181 | 0 | 0 | 0 | 0 | 0 | 0 |
| TPAVGRLEV | B*42:01 | 200 | 0 | 0 | 0 | 0 | 0 | 0 |
| FAQIISVALI | C*12:03 | 43 | 0 | 0 | 0 | 0 | 0 | 0 |
| FAYPAIRYL | C*12:03 | 44 | 0 | 0 | 0 | 0 | 0 | 0 |
| FVFPGELLL | C*12:03 | 51 | 0 | 0 | 0 | 0 | 0 | 0 |
| VPLPPKGRVL | C*12:03 | 210 | 0 | 0 | 0 | 0 | 0 | 0 |
| LAFPGEMLL | A*02:01 | 107 | 0 | 0 | 0 | 0 | 0 | 0 |
| APRHPSTNSL | B*42:01 | 13 | 0 | 0 | 1 | 0 | 0 | 0 |

TABLE 5A-continued

Myeloma-associated peptides as detected on MM.1S cells and their modulation upon carfilzomib-treatment

| Myeloma LiTAP | HLA | SEQ ID NO | 24#1 | 24#2 | 24#3 | 48#1 | 48#2 | 48#3 |
|---|---|---|---|---|---|---|---|---|
| RPKAQPTTL | B*42:01 | 150 | 0 | 0 | 1 | 0 | 0 | 0 |
| TASPLVKSV | C*12:03 | 193 | 0 | 0 | 0 | 0 | 1 | 0 |
| NEVIMTIGF | B*18:01 | 129 | 0 | 0 | 0 | 0 | 1 | 0 |
| EYGHIPSF | A*24:02 | 42 | 1 | 1 | 0 | 0 | 0 | 0 |
| TPSSRPASL | B*42:01 | 202 | 1 | 1 | 0 | 0 | 0 | 0 |
| KPQPRPQTL | C*12:03 | 94 | 1 | 1 | 1 | 0 | 0 | 0 |
| KPRPPQGL | B*42:01 | 95 | 1 | 1 | 1 | 1 | 0 | 0 |
| IEHPSMSVY | B*18:01 | 69 | 1 | 1 | 1 | 0 | 1 | 1 |
| VPLTRVSGGAA | B*42:01 | 211 | 1 | 1 | 1 | 1 | 1 | 1 |

Legend: 24#1-time after carfilzomib treatment/biological replicate
-1 significantly down-modulated
0 not significantly/not detected
1 significantly up-modulated

TABLE 5B

Myeloma-associated peptides as detected on U266 cells and their modulation upon carfilzomib-treatment

| Myeloma LiTAP | HLA | SEQ ID NO | 24#1 | 24#2 | 24#3 | 48#1 | 48#2 | 48#3 |
|---|---|---|---|---|---|---|---|---|
| KAMEAASSL | B*07:02 | 82 | -1 | -1 | -1 | -1 | -1 | -1 |
| KPKDPLKISL | B*07:02 | 93 | -1 | -1 | -1 | 0 | -1 | -1 |
| RVFPYSVFY | A*03:01 | 158 | -1 | 0 | 0 | -1 | -1 | -1 |
| SRGDFVVEY | C*07:02 | 190 | 0 | -1 | 0 | 0 | 0 | -1 |
| IIFDRPLLY | A*03:01 | 73 | 0 | 0 | 0 | 0 | 0 | -1 |
| SVYSPVKKK | A*03:01 | 191 | 0 | 0 | -1 | 0 | 0 | 0 |
| GEVQDLLVRL | B*40:01 | 56 | 0 | 0 | 0 | 0 | 0 | 0 |
| KAVNPGRSL | B*07:02 | 83 | 0 | 0 | 0 | 0 | 0 | 0 |
| SPRLSLLYL | B*07:02 | 186 | 0 | 0 | 0 | 0 | 0 | 0 |
| ILRDGITAGK | A*03:01 | 74 | 0 | 0 | 0 | 0 | 0 | 0 |
| RVAKTNSLR | A*03:01 | 157 | 0 | 0 | 0 | 0 | 0 | 0 |
| TPAVGRLEV | B*07:02 | 200 | 0 | 0 | 0 | 0 | 0 | 0 |
| SPALKRLDL | B*07:02 | 180 | 0 | 0 | 0 | 0 | 0 | 0 |
| SPRQALTDF | B*07:02 | 187 | 0 | 0 | 0 | 0 | 0 | 0 |
| AEQEIARLVL | B*40:01 | 3 | 0 | 0 | 0 | 0 | 0 | 0 |
| KILKPVKKK | A*03:01 | 88 | 0 | 0 | 0 | 0 | 0 | 0 |
| ALWGRTTLK | A*03:01 | 10 | 0 | 0 | 0 | 0 | 0 | 0 |
| KPQPRPQTL | B*07:02 | 94 | 0 | 0 | 0 | 0 | 0 | 0 |
| RVNKVIIGTK | A*03:01 | 159 | 0 | 0 | 0 | 0 | 0 | 0 |
| ILWETVPSM | A*02:01 | 75 | 0 | 0 | 0 | 0 | 0 | 0 |
| RPGPPTRPL | B*07:02 | 148 | 0 | 0 | 0 | 0 | 0 | 0 |

TABLE 5B-continued

Myeloma-associated peptides as detected on U266 cells and their modulation upon carfilzomib-treatment

| Myeloma LiTAP | HLA | SEQ ID NO | 24#1 | 24#2 | 24#3 | 48#1 | 48#2 | 48#3 |
|---|---|---|---|---|---|---|---|---|
| SESLPVRTL | B*40:01 | 167 | 0 | 0 | 0 | 0 | 0 | 0 |
| KLPLPLPPRL | A*02:01 | 90 | 0 | 0 | 0 | 0 | 0 | 0 |
| YLYITKVLK | A*03:01 | 221 | 0 | 0 | 0 | 0 | 0 | 0 |
| KTEVHIRPK | A*03:01 | 100 | 0 | 0 | 0 | 0 | 0 | 0 |
| PELGPLPAL | B*40:01 | 135 | 0 | 0 | 0 | 0 | 0 | 0 |
| RPKAQPTTL | B*07:02 | 150 | 0 | 0 | 0 | 0 | 0 | 0 |
| FLWDEGFHQL | A*02:01 | 49 | 0 | 0 | 0 | 0 | 0 | 0 |
| RPFHGVVTSL | B*07:02 | 147 | 0 | 0 | 0 | 0 | 0 | 0 |
| RQFVVTRTKK | A*03:01 | 155 | 0 | 0 | 0 | 0 | 0 | 0 |
| RPQLKGVVL | B*07:02 | 151 | 0 | 0 | 0 | 0 | 0 | 0 |
| IESHPDNAL | B*40:01 | 70 | 0 | 0 | 0 | 0 | 0 | 0 |
| REEGTPLTL | B*40:01 | 141 | 0 | 0 | 0 | 0 | 0 | 0 |
| GEVAPSMFL | B*40:01 | 55 | 0 | 0 | 0 | 0 | 0 | 0 |
| SPYLRPLTL | B*07:02 | 189 | 0 | 0 | 0 | 0 | 0 | 0 |
| KPSTKALVL | B*07:02 | 97 | 0 | 0 | 0 | 0 | 0 | 0 |
| KLSSLIILM | A*02:01 | 92 | 0 | 0 | 0 | 0 | 0 | 0 |
| LPPPPHVPL | B*07:02 | 115 | 0 | 0 | 0 | 0 | 0 | 0 |
| GETAFAFHL | B*40:01 | 54 | 0 | 0 | 0 | 0 | 0 | 0 |
| LLFPYILPPK | A*03:01 | 111 | 0 | 0 | 0 | 0 | 0 | 0 |
| IPAKPPVSF | B*07:02 | 76 | 0 | 0 | 0 | 0 | 0 | 0 |
| GPRPITQSEL | B*07:02 | 61 | 0 | 0 | 0 | 0 | 0 | 0 |
| TPSSRPASL | B*07:02 | 202 | 0 | 0 | 0 | 0 | 0 | 0 |
| RPRPPVLSV | B*07:02 | 154 | 0 | 0 | 0 | 0 | 0 | 0 |
| KEGLILPETL | B*40:01 | 87 | 1 | 1 | 0 | 0 | 0 | 0 |
| FAYPAIRYL | A*02:01 | 44 | 0 | 0 | 0 | 1 | 0 | 1 |
| FVFPGELLL | A*02:01 | 51 | 1 | 1 | 0 | 0 | 0 | 0 |
| APFQGDQRSL | B*07:02 | 11 | 0 | 1 | 1 | 0 | 1 | 0 |
| KPRPPQGL | B*07:02 | 95 | 0 | 0 | 0 | 1 | 1 | 1 |
| APRHPSTNSLL | B*07:02 | 14 | 0 | 1 | 0 | 1 | 1 | 0 |
| APRHPSTNSL | B*07:02 | 13 | 0 | 1 | 0 | 1 | 1 | 0 |

Legend: 24#1-time after carfilzomib treatment/biological replicate
-1 significantly down-modulated
0 not significant/not detected
1 significantly up-modulated The MM.1S model was then used to longitudinally track the abundances of the 14/31 myeloma peptides for which quantitative information was available across all time points and conditions. For the majority of these targets (10/14, 71.4%), we observed a peak in modulation at t24 h followed by a gradual decline toward baseline levels at t48 h. Only 4/14 peptides (28.6%) showed persistent modulation even at t48 h, with three of them showing progressive down-modulation after treatment.

Amongst others, SEQ ID NO: 42: showed a significant up-modulation on MM.1s cells 24 h after carfilzomib treatment in 2/3 biological replicates. In contrast, no significant modulation upon carfilzomib treatment was found on MM.1S for SEQ ID NO: 107 and SEQ ID NO: 228.

CITED REFERENCES

1. Small, E. J., et al., *Placebo-controlled phase III trial of immunologic therapy with sipuleucel-T (APC8015) in patients with metastatic, asymptomatic hormone refractory prostate cancer.* J Clin Oncol, 2006. 24(19): p. 3089-94.
2. Walter, S., et al., *Multipeptide immune response to cancer vaccine IMA901 after single-dose cyclophosphamide associates with longer patient survival.* Nat Med, 2012.
3. Perez-Gracia, J. L., et al., *Orchestrating immune checkpoint blockade for cancer immunotherapy in combinations.* Curr Opin Immunol, 2014. 27: p. 89-97.
4. van Rooij, N., et al., *Tumor exome analysis reveals neoantigen-specific T-cell reactivity in an ipilimumab-responsive melanoma.* J Clin Oncol, 2013. 31(32): p. e439-42.
5. Robbins, P. F., et al., *Mining exomic sequencing data to identify mutated antigens recognized by adoptively transferred tumor-reactive T cells.* Nat Med, 2013. 19(6): p. 747-52.
6. Tran, E., et al., *Cancer immunotherapy based on mutation-specific CD4+ T cells in a patient with epithelial cancer.* Science, 2014. 344(6184): p. 641-5.
7. Schumacher, T., et al., *A vaccine targeting mutant IDH1 induces antitumour immunity.* Nature, 2014. 512(7514): p. 324-7.
8. Snyder, A., et al., *Genetic basis for clinical response to CTLA-4 blockade in melanoma.* N Engl J Med, 2014. 371(23): p. 2189-99.
9. Snyder, A. and T. A. Chan, *Immunogenic peptide discovery in cancer genomes.* Curr Opin Genet Dev, 2015. 30C: p. 7-16.
10. Rizvi, N. A., et al., *Mutational landscape determines sensitivity to PD-1 blockade in non-small cell lung cancer.* Science, 2015.
11. Linnemann, C., et al., *High-throughput epitope discovery reveals frequent recognition of neo-antigens by CD4+ T cells in human melanoma.* Nat Med, 2015. 21(1): p. 81-5.
12. Berlin, C., et al., *Mapping the HLA ligandome landscape of acute myeloid leukemia: a targeted approach toward peptide-based immunotherapy.* Leukemia, 2014.
13. Kowalewski, D. J., et al., *HLA ligandome analysis identifies the underlying specificities of spontaneous anti-leukemia immune responses in chronic lymphocytic leukemia (CLL).* Proc Natl Acad Sci USA, 2014.
14. Kuehl, W. M. and P. L. Bergsagel, *Multiple myeloma: evolving genetic events and host interactions.* Nat Rev Cancer, 2002. 2(3): p. 175-87.
15. Rollig, C., S. Knop, and M. Bornhauser, *Multiple myeloma.* Lancet, 2014.
16. Barlogie, B., et al., *Long-term outcome results of the first tandem autotransplant trial for multiple myeloma.* Br J Haematol, 2006. 135(2): p. 158-64.
17. Ferrero, S., et al., *Long-term results of the GIMEMA VEL-03-096 trial in MM patients receiving VTD consolidation after ASCT: MRD kinetics' impact on survival.* Leukemia, 2014.
18. Martinez-Lopez, J., et al., *Prognostic value of deep sequencing method for minimal residual disease detection in multiple myeloma.* Blood, 2014. 123(20): p. 3073-9.
19. Bjorkstrand, B., et al., *Tandem autologous/reduced-intensity conditioning allogeneic stem-cell transplantation versus autologous transplantation in myeloma: long-term follow-up.* J Clin Oncol, 2011. 29(22): p. 3016-22.
20. El-Cheikh, J., et al., *Long-term outcome after allogeneic stem-cell transplantation with reduced-intensity conditioning in patients with multiple myeloma.* Am J Hematol, 2013. 88(5): p. 370-4.
21. Koehne, G. and S. Giralt, *Allogeneic hematopoietic stem cell transplantation for multiple myeloma: curative but not the standard of care.* Curr Opin Oncol, 2012. 24(6): p. 720-6.
22. Riley, J. L., *Combination checkpoint blockade—taking melanoma immunotherapy to the next level.* N Engl J Med, 2013. 369(2): p. 187-9.
23. Perez, S. A., et al., *A new era in anticancer peptide vaccines.* Cancer, 2010. 116(9): p. 2071-80.
24. Rosenblatt, J., et al., *Immunotherapy for multiple myeloma.* Expert Rev Hematol, 2014. 7(1): p. 91-6.
25. Brossart, P., et al., *The epithelial tumor antigen MUC1 is expressed in hematological malignancies and is recognized by MUC1-specific cytotoxic T-lymphocytes.* Cancer Res, 2001. 61(18): p. 6846-50.
26. Zhou, F. L., et al., *Peptide-based immunotherapy for multiple myeloma: current approaches.* Vaccine, 2010. 28(37): p. 5939-46.
27. Hundemer, M., et al., *Identification of a new HLA-A2-restricted T-cell epitope within HM1.24 as immunotherapy target for multiple myeloma.* Exp Hematol, 2006. 34(4): p. 486-96.
28. Jalili, A., et al., *Induction of HM1.24 peptide-specific cytotoxic T lymphocytes by using peripheral-blood stem-cell harvests in patients with multiple myeloma.* Blood, 2005. 106(10): p. 3538-45.
29. Chiriva-Internati, M., et al., *Testing recombinant adeno-associated virus-gene loading of dendritic cells for generating potent cytotoxic T lymphocytes against a prototype self-antigen, multiple myeloma HM1.24.* Blood, 2003. 102(9): p. 3100-7.
30. Rew, S. B., et al., *Generation of potent antitumor CTL from patients with multiple myeloma directed against HM1.24.* Clin Cancer Res, 2005. 11(9): p. 3377-84.
31. van Rhee, F., et al., *NY-ESO-1 is highly expressed in poor-prognosis multiple myeloma and induces spontaneous humoral and cellular immune responses.* Blood, 2005. 105(10): p. 3939-44.
32. Schuberth, P. C., et al., *Effector memory and central memory NY-ESO-1-specific re-directed T cells for treatment of multiple myeloma.* Gene Ther, 2013. 20(4): p. 386-95.
33. Bae, J., et al., *Novel epitope evoking CD138 antigen-specific cytotoxic T lymphocytes targeting multiple myeloma and other plasma cell disorders.* Br J Haematol, 2011. 155(3): p. 349-61.
34. Bae, J., et al., *Identification of novel myeloma-specific XBP1 peptides able to generate cytotoxic T lymphocytes: a potential therapeutic application in multiple myeloma.* Leukemia, 2011. 25(10): p. 1610-9.
35. Bae, J., et al., *Myeloma-specific multiple peptides able to generate cytotoxic T lymphocytes: a potential therapeutic application in multiple myeloma and other plasma cell disorders.* Clin Cancer Res, 2012. 18(17): p. 4850-60.
36. Oka, Y., et al., *WT1 peptide vaccine as a paradigm for "cancer antigen-derived peptide"-based immunotherapy for malignancies: successful induction of anti-cancer effect by vaccination with a single kind of WT1 peptide.* Anticancer Agents Med Chem, 2009. 9(7): p. 787-97.
37. Kuball, J., et al., *Pitfalls of vaccinations with WT1-, Proteinase3- and MUC1-derived peptides in combination* with MontanideISA51 and CpG7909. Cancer Immunol Immunother, 2011. 60(2): p. 161-71.
38. Greiner, J., et al., *High-dose RHAMM-R3 peptide vaccination for patients with acute myeloid leukemia, myelodysplastic syndrome and multiple myeloma*. Haematologica, 2010. 95(7): p. 1191-7.
39. Schmitt, M., et al., *RHAMM-R3 peptide vaccination in patients with acute myeloid leukemia, myelodysplastic syndrome, and multiple myeloma elicits immunologic and clinical responses*. Blood, 2008. 111(3): p. 1357-65.
40. Rapoport, A. P., et al., *Combination immunotherapy using adoptive T-cell transfer and tumor antigen vaccination on the basis of hTERT and survivin after ASCT for myeloma*. Blood, 2011. 117(3): p. 788-97.
41. Hobo, W., et al., *Immunogenicity of dendritic cells pulsed with MAGE3, Survivin and B-cell maturation antigen mRNA for vaccination of multiple myeloma patients*. Cancer Immunol Immunother, 2013. 62(8): p. 1381-92.
42. Wang, L., et al., *T cell-based targeted immunotherapies for patients with multiple myeloma*. Int J Cancer, 2014.
43. Goswami, M., et al., *Expression of putative targets of immunotherapy in acute myeloid leukemia and healthy tissues*. Leukemia, 2014. 28(5): p. 1167-70.
44. Kowalewski, D. J. and S. Stevanovic, *Biochemical large-scale identification of MHC class I ligands*. Methods Mol Biol, 2013. 960: p. 145-57.
45. Kall, L., et al., *Semi-supervised learning for peptide identification from shotgun proteomics datasets*. Nat Methods, 2007. 4(11): p. 923-5.
46. Schuler, M. M., M. D. Nastke, and S. Stevanovikc, *SYFPEITHI: database for searching and T-cell epitope prediction*. Methods Mol Biol, 2007. 409: p. 75-93.
47. Sturm, T., et al., *Mouse urinary peptides provide a molecular basis for genotype discrimination by nasal sensory neurons*. Nat Commun, 2013. 4: p. 1616.
48. Garboczi, D. N., D. T. Hung, and D. C. Wiley, *HLA-A2-peptide complexes: refolding and crystallization of molecules expressed in Escherichia coli and complexed with single antigenic peptides*. Proc Natl Acad Sci USA, 1992. 89(8): p. 3429-33.
49. Widenmeyer, M., et al., *Promiscuous survivin peptide induces robust CD4+ T-cell responses in the majority of vaccinated cancer patients*. Int J Cancer, 2012. 131(1): p. 140-9.
50. Britten, C. M., et al., *The CIMT-monitoring panel: a two-step approach to harmonize the enumeration of antigen-specific CD8+ T lymphocytes by structural and functional assays*. Cancer Immunol Immunother, 2008. 57(3): p. 289-302.
51. Rudolf, D., et al., *Potent costimulation of human CD8 T cells by anti-4-1BB and anti-CD28 on synthetic artificial antigen presenting cells*. Cancer Immunol Immunother, 2008. 57(2): p. 175-83.
52. Bui, H. H., et al., *Predicting population coverage of T-cell epitope-based diagnostics and vaccines*. BMC Bioinformatics, 2006. 7: p. 153.
53. Schipper, R. F., et al., *Minimal phenotype panels. A method for achieving maximum population coverage with a minimum of HLA antigens*. Hum Immunol, 1996. 51(2): p. 95-8.
54. Kanehisa, M. and S. Goto, *KEGG: kyoto encyclopedia of genes and genomes*. Nucleic Acids Res, 2000. 28(1): p. 27-30.
55. Huang da, W., B. T. Sherman, and R. A. Lempicki, *Systematic and integrative analysis of large gene lists using DAVID bioinformatics resources*. Nat Protoc, 2009. 4(1): p. 44-57.
56. Braumuller, H., et al., *T-helper-1-cell cytokines drive cancer into senescence*. Nature, 2013. 494(7437): p. 361-5.
57. Schoenberger, S. P., et al., *T-cell help for cytotoxic T lymphocytes is mediated by CD40-CD40L interactions*. Nature, 1998. 393(6684): p. 480-3.
58. Janssen, E. M., et al., $CD4^+$ *T cells are required for secondary expansion and memory in* $CD8^+$ *T lymphocytes*. Nature, 2003. 421(6925): p. 852-6.
59. Greiner, J., et al., *Mutated regions of nucleophosmin 1 elicit both CD4(+) and CD8(+) T-cell responses in patients with acute myeloid leukemia*. Blood, 2012. 120 (6): p. 1282-9.
60. Wolchok, J. D., et al., *Nivolumab plus ipilimumab in advanced melanoma*. N Engl J Med, 2013. 369(2): p. 122-33.
61. Topalian, S. L., et al., *Safety, activity, and immune correlates of anti-PD-1 antibody in cancer*. N Engl J Med, 2012. 366(26): p. 2443-54.
62. Hodi, F. S., et al., *Improved survival with ipilimumab in patients with metastatic melanoma*. N Engl J Med, 2010. 363(8): p. 711-23.
63. Robert, C., et al., *Anti-programmed-death-receptor-1 treatment with pembrolizumab in ipilimumab-refractory advanced melanoma: a randomised dose-comparison cohort of a phase 1 trial*. Lancet, 2014. 384(9948): p. 1109-17.
64. Brahmer, J. R., et al., *Safety and activity of anti-PD-L1 antibody in patients with advanced cancer*. N Engl J Med, 2012. 366(26): p. 2455-65.
65. Hamid, O., et al., *Safety and tumor responses with lambrolizumab (anti-PD-1) in melanoma*. N Engl J Med, 2013. 369(2): p. 134-44.
66. Motzer, R. J., et al., *Nivolumab for Metastatic Renal Cell Carcinoma: Results of a Randomized Phase II Trial*. J Clin Oncol, 2014.
67. Lynch, T. J., et al., *Ipilimumab in combination with paclitaxel and carboplatin as first-line treatment in stage IIIB/IV non-small-cell lung cancer: results from a randomized, double-blind, multicenter phase II study*. J Clin Oncol, 2012. 30(17): p. 2046-54.
68. Ansell, S. M., et al., *Phase I study of ipilimumab, an anti-CTLA-4 monoclonal antibody, in patients with relapsed and refractory B-cell non-Hodgkin lymphoma*. Clin Cancer Res, 2009. 15(20): p. 6446-53.
69. Ansell, S. M., et al., *PD-1 blockade with nivolumab in relapsed or refractory Hodgkin's lymphoma*. N Engl J Med, 2015. 372(4): p. 311-9.
70. Bassani-Sternberg, M., et al., *Mass spectrometry of human leukocyte antigen class I peptidomes reveals strong effects of protein abundance and turnover on antigen presentation*. Mol Cell Proteomics, 2015. 14(3): p. 658-73.
71. Stickel, J. S., et al., *HLA ligand profiles of primary renal cell carcinoma maintained in metastases*. Cancer Immunol Immunother, 2009. 58(9): p. 1407-17.
72. Weinzierl, A. O., et al., *Distorted relation between mRNA copy number and corresponding major histocompatibility complex ligand density on the cell surface*. Mol Cell Proteomics, 2007. 6(1): p. 102-13.
73. Min, D. J., et al., *MMSET stimulates myeloma cell growth through microRNA-mediated modulation of c-MYC*. Leukemia, 2013. 27(3): p. 686-94.

74. Martinez-Garcia, E., et al., *The MMSET histone methyl transferase switches global histone methylation and alters gene expression in t(4;14) multiple myeloma cells*. Blood, 2011. 117(1): p. 211-20.
75. Keats, J. J., et al., *Overexpression of transcripts originating from the MMSET locus characterizes all t(4;14) (p16;q32)-positive multiple myeloma patients*. Blood, 2005. 105(10): p. 4060-9.
76. Brito, J. L., et al., *MMSET deregulation affects cell cycle progression and adhesion regulons in t(4;14) myeloma plasma cells*. Haematologica, 2009. 94(1): p. 78-86.
77. Smith, E. M., K. Boyd, and F. E. Davies, *The potential role of epigenetic therapy in multiple myeloma*. Br J Haematol, 2010. 148(5): p. 702-13.
78. Xie, Z., et al., *Plasma membrane proteomics identifies biomarkers associated with MMSET overexpression in T(4;14) multiple myeloma*. Oncotarget, 2013. 4(7): p. 1008-18.
79. Hebraud, B., et al., *The translocation t(4;14) can be present only in minor subclones in multiple myeloma*. Clin Cancer Res, 2013. 19(17): p. 4634-7.

---

The invention claimed is:

1. A method of eliciting an immune response in a patient who has cancer, comprising administering to the patient a composition comprising a population of activated T cells that selectively recognize cancer cells that present a peptide consisting of an amino acid sequence selected from SEQ ID NO: 1 to SEQ ID NO: 5 or SEQ ID NO: 7 to SEQ ID NO: 10,
wherein the activated T cells are produced by contacting T cells with the peptide loaded onto a human class I MEW molecule expressed on the surface of an antigen-presenting cell for a period of time sufficient to activate the T cells,
wherein said cancer is selected from lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, and bile duct cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the peptide is in a complex with the class I MEW molecule.

7. The method of claim 1, wherein the antigen presenting cell is infected with recombinant virus expressing the peptide.

8. The method of claim 7, wherein the antigen presenting cell is a dendritic cell or a macrophage.

9. The method of claim 5, wherein the expansion is in the presence of an anti-CD28 antibody and IL-12.

10. The method of claim 1, wherein the population of activated T cells comprises CD8-positive cells.

11. The method of claim 1, wherein the contacting is in vitro.

12. The method of claim 1, wherein the composition further comprises an adjuvant.

13. The method of claim 12, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, and particulate formulations with poly(lactide co-glycolide) (PLG), virosomes, interleukin (IL)-1, IL-2, IL-4, IL-7, IL-12, IL-13, IL-15, IL-21, and IL-23.

14. The method of claim 1, wherein the immune response comprises a cytotoxic T cell response.

15. A method of killing cancer cells, comprising performing the method of eliciting an immune response of claim 1, wherein the cancer cells are killed.

16. The method of claim 15, wherein the immune response comprises a cytotoxic T cell response.

17. The method of claim 1, wherein said amino acid sequence consists of SEQ ID NO: 1.

18. The method of claim 1, wherein said amino acid sequence consists of SEQ ID NO: 2.

19. The method of claim 1, wherein said amino acid sequence consists of SEQ ID NO: 3.

20. The method of claim 1, wherein said amino acid sequence consists of SEQ ID NO: 4.

21. The method of claim 1, wherein said amino acid sequence consists of SEQ ID NO: 5.

22. The method of claim 1, wherein said amino acid sequence consists of SEQ ID NO: 7.

23. The method of claim 1, wherein said amino acid sequence consists of SEQ ID NO: 8.

24. The method of claim 1, wherein said amino acid sequence consists of SEQ ID NO: 9.

25. The method of claim 1, wherein said amino acid sequence consists of SEQ ID NO: 10.

* * * * *